US010667762B2

(12) United States Patent
Barker et al.

(10) Patent No.: US 10,667,762 B2
(45) Date of Patent: *Jun. 2, 2020

(54) MODULAR MULTI-PARAMETER PATIENT MONITORING DEVICE

(71) Applicant: Masimo Corporation, Irvine, CA (US)

(72) Inventors: Nicholas Evan Barker, Laguna Beach, CA (US); Chad A. DeJong, Los Angeles, CA (US); Kirby Clark Dotson, Temecula, CA (US); Ammar Al-Ali, San Juan Capistrano, CA (US); Bilal Muhsin, San Clemente, CA (US); Sujin Hwang, Irvine, CA (US); Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/409,625

(22) Filed: May 10, 2019

(65) Prior Publication Data
US 2020/0000415 A1   Jan. 2, 2020

Related U.S. Application Data

(63) Continuation of application No. 15/903,526, filed on Feb. 23, 2018, now Pat. No. 10,327,713.
(Continued)

(51) Int. Cl.
A61B 5/00    (2006.01)
G16H 30/40   (2018.01)
(Continued)

(52) U.S. Cl.
CPC .......... A61B 5/7425 (2013.01); G06F 1/1601 (2013.01); G06F 1/181 (2013.01);
(Continued)

(58) Field of Classification Search
CPC ............ A61B 5/7425; A61B 2560/045; A61B 2560/0456; G16H 30/40; G16H 40/63;
(Continued)

(56) References Cited

U.S. PATENT DOCUMENTS 4,960,128 A   10/1990 Gordon et al.
4,964,408 A   10/1990 Hink et al.
(Continued)

Primary Examiner — Sisay Yacob
(74) Attorney, Agent, or Firm — Knobbe, Martens, Olson & Bear, LLP

(57) ABSTRACT

A multi-parameter patient monitoring device rack can dock a plurality of patient monitor modules and can communicate with a separate display unit. A signal processing unit can be incorporated into the device rack. A graphics processing unit can be attached to the display unit. The device rack and the graphic display unit can have improved heat dissipation and drip-proof features. The multi-parameter patient monitoring device rack can provide interchangeability and versatility to a multi-parameter patient monitoring system by allowing use of different display units and monitoring of different combinations of parameters. A dual-use patient monitor module can have its own display unit configured for displaying one or more parameters when used as a stand-alone device, and can be docked into the device rack when a handle on the module is folded down.

20 Claims, 33 Drawing Sheets

Related U.S. Application Data

(60) Provisional application No. 62/463,297, filed on Feb. 24, 2017.

(51) Int. Cl.
| | | |
|---|---|---|
| *G06T 1/20* | (2006.01) | |
| *H05K 5/02* | (2006.01) | |
| *H05K 7/20* | (2006.01) | |
| *H05K 5/00* | (2006.01) | |
| *H05K 7/18* | (2006.01) | |
| *G06F 1/20* | (2006.01) | |
| *G06F 1/18* | (2006.01) | |
| *G16H 40/63* | (2018.01) | |
| *G06F 1/16* | (2006.01) | |

(52) U.S. Cl.
CPC .............. *G06F 1/20* (2013.01); *G06T 1/20* (2013.01); *G16H 30/40* (2018.01); *G16H 40/63* (2018.01); *H05K 5/0017* (2013.01); *H05K 5/0213* (2013.01); *H05K 7/18* (2013.01); *H05K 7/20136* (2013.01); *H05K 7/20172* (2013.01); *A61B 2560/045* (2013.01); *A61B 2560/0456* (2013.01); *G06F 2200/201* (2013.01)

(58) Field of Classification Search
CPC ....... G06F 1/20; G06F 2200/201; G06T 1/20; H05K 5/0017; H05K 5/0213; H05K 7/18; H05K 7/20136; H05K 7/20172
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |

(56) References Cited

U.S. PATENT DOCUMENTS

| | | |
|---|---|---|
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |

(56) References Cited

U.S. PATENT DOCUMENTS

| | | | |
|---|---|---|---|
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |

(56) References Cited

U.S. PATENT DOCUMENTS

| | | |
|---|---|---|
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |

(56) References Cited

U.S. PATENT DOCUMENTS

| | | |
|---|---|---|
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 2006/0148398 A1* | 7/2006 | Ruch .......... H05K 5/0213 454/184 |
| 2006/0161054 A1 | 7/2006 | Reuss et al. |
| 2007/0282478 A1 | 12/2007 | Al-Ali et al. |
| 2009/0124868 A1* | 5/2009 | Barnett .......... A61N 1/3968 600/301 |
| 2009/0247984 A1 | 10/2009 | Lamego et al. |
| 2009/0275813 A1 | 11/2009 | Davis |

(56) References Cited

U.S. PATENT DOCUMENTS

| | | |
|---|---|---|
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |

(56) References Cited

U.S. PATENT DOCUMENTS

| | | |
|---|---|---|
| 2018/0069776 A1 | 3/2018 | Lamego et al. |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali |
| 2019/0357812 A1 | 11/2019 | Poeze et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000340 A1 | 1/2020 | Wojtczuk et al. |
| 2020/0000415 A1 | 1/2020 | Barker et al. |

* cited by examiner

MODULAR MULTI-PARAMETER PATIENT MONITORING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application is a continuation of U.S. patent application Ser. No. 15/903,526, filed Feb. 23, 2018, entitled "MODULAR MULTI-PARAMETER PATIENT MONITORING DEVICE", which claims priority benefit of U.S. Provisional Application No. 62/463,297, filed Feb. 24, 2017, titled "MODULAR MULTI-PARAMETER PATIENT MONITORING DEVICE," incorporated herein by reference in its entirety.

FIELD OF THE DISCLOSURE

The present disclosure relates to patient monitoring. In particular, the present disclosure relates to multi-parameter patient monitoring technology.

BACKGROUND

Patient care often requires monitoring of a number of parameters, including but are not limited to Oxygen Saturation (SpO2), Pulse Rate (PR), Perfusion Index (PI), Total Hemoglobin (SpHb), Oxygen Content (SpOC), Pleth Variability Index (PVI®), Methemoglobin (SpMet), Carboxyhemoglobin (SpCO), Respiration Rate (RR), noninvasive blood pressure (NBP), EEG, EKG and the like. Multi-parameter patient monitoring systems, for example, the Root® Patient Monitoring and Connectivity Platform of Masimo (Irvine, Calif.), can simultaneously measure and display relevant vital parameters, and can be integrated into the hospital bedside monitors and/or the anesthetic machines in operating rooms.

Multi-parameter patient monitoring systems can have a docking station or a device rack configured to receive a plurality of patient monitor processing modules. The docking station can provide basic connectivity between the one or more patient monitor modules or sensors and the processing components, and may not have its own processing unit for processing the signals from the one or more modules or sensors. The processing components can process patient data received from the patient monitor modules. The processing components can often be integrated with a display device. The monitoring system can also have a graphics processing unit for displaying at least a portion of the patient data on the display device. The patient monitor modules can have a sensor port for receiving a physiological sensor. The patient monitor modules can have their own signal and graphics processors and display screens so as to be used as portable patient monitor devices.

SUMMARY

Heat management may not be a big concern in traditional multi-parameter patient monitoring systems, which do not require a powerful graphics processing unit as the parameters being displayed include mostly numbers and simple charts. It is becoming more desirable to have multi-parameter patient monitoring systems become increasingly more capable of displaying graphic-rich contents, such as animations and simulations, including three-dimensional simulations. However, more graphic-rich graphics processing units have not been incorporated in current multi-parameter patient monitoring systems because the more graphic-rich graphics processing units create significant heat that can be difficult to dissipate. The present disclosure provides a multi-parameter patient monitoring system incorporating a graphic-rich graphics processing unit by solving the heat dissipation issue.

Current multi-parameter patient monitoring systems typically have the signal processing unit and graphics processing unit located in the same housing. Heat can be accumulated quickly within the housing when the patient monitoring system is in use even in systems that use low-capability graphics processing units. A more graphic-rich graphics processing unit can generate a higher amount of heat when in use causing significantly more heat build-up and potentially damaging the system. Heat accumulated inside the housing needs to be effectively dissipated to avoid overheating of the electrical circuitry. Typical vent openings, such as those located on one side of the housing, are inadequate. More vent openings and/or bigger vent openings, and/or bigger fans may be needed to allow more air to enter the housing for cooling the processor. Fans capable of pulling sufficient air flow through vents are often loud and a nuisance. More and/or bigger openings can make the housing of the processing unit less effective at muffling the sound noise from the fans.

Furthermore, vent openings large enough to effectively dissipate heat generated by both the signal processing unit and the graphics processing unit would open the processing components to contamination or damage from the hospital environment. Liquids, such as IV drips, disinfecting solutions, and/or others, can enter into the housing from the vent openings. Exposure of electrical circuits inside the monitoring system housing to liquid can result in short-circuiting, malfunctioning of the monitoring system, and/or endanger the safety of the healthcare personnel and/or the patient due to electric shock.

Current multi-parameter patient monitoring systems are also often bulky and difficult to move because of the integrated display device. Typical multi-parameter patient monitors with integrated displays do not allow for interchangeable patient monitor processing modules of different sizes and configurations. For example, patients in a step-down unit may have more mobility than patients in an intensive care unit (ICU), and may not need to be monitored on a large number of parameters. These patients may also not want their movements restricted by the cables connecting the patients to the bulky patient monitoring system. It would be advantageous for patients in the step-down unit to have a wearable monitoring device with a small display device. As an alternative example, patients in the ICU may require extensive monitoring of their vital parameters and a large display device can provide more room for displaying a multitude of parameters and/or charts. While it is possible to have monitors with two different sized displays, it is expensive for hospitals to keep two sizes of the patient monitoring systems and demand for each size of the patient monitoring systems may be unpredictable.

The current monitoring systems also typically have a predetermined set of sensor ports such that the types of parameters that the current monitoring systems are able to measure and display cannot be customized based on the use. Different patient care settings can require monitoring of different parameters, requiring multiple different types of monitoring systems. For example, patients in the ICU may require monitoring of a large number of parameters, including nitric oxide, brain activities and the like, whereas patients in a less acute condition, such as in a step-down unit or an emergency room, may only need to be monitored for a subset of basic parameters. It is expensive and impractical to manufacture a multi-parameter patient monitoring system that offers all possible combinations of parameters. It is also expensive for hospitals to have to keep patient monitoring systems with different combinations of parameter measuring capabilities.

In addition, manufacturers of current patient monitoring systems commonly provide compatibility among sensors and/or processing components from the same manufacturer. These systems may be incompatible with third party sensors and/or processing components, thereby limiting the scope of parameters that a multi-parameter patient monitoring system can display.

Some small patient monitoring devices, such as the patient monitor modules, can potentially be used as either a stand-alone device or docked into a docking station of a multi-patient monitoring system as a module. However, some small patient monitoring devices may not have the brick-like overall shape in order to fit into the docking station. For example, portable patient monitoring devices can commonly have a handle for ease of being carried around. The handle prevents the patient monitoring devices from being able to fit into a docking station of a multi-parameter patient monitoring system. Patient monitor modules can have a shape suitable for being received by a docking station, but may not have handles. These patient monitor modules can thus lack portability as it can be inconvenient to hand-carry the modules to different locations in a hospital.

The present disclosure provides example multi-parameter patient monitoring systems that remedy those technical problems of current multi-parameter patient monitoring devices and/or other problems. The present disclosure includes a multi-parameter patient monitoring system having a display unit with a graphics processing unit attached, and a device rack including a signal processing unit enclosed by a device rack housing. The graphics processing unit can have a housing with vent openings for heat dissipation and/or a drip-proof outer shell to shield the vent openings from fluid without blocking an air flow path through the vent openings. The device rack can be configured to dock a plurality of patient monitor modules and can communicate with the separate display unit. The device rack can also have an improved air flow path to dissipate heat in the device rack and/or drip-proof features. The patient monitor modules can be coupled with one or more sensors, and have their own processing units and optionally their own display screens. The device rack can also have vent openings to allow the improved air flow to cool the processing units of the patient monitor modules. The modules can be third party patient monitoring modules or "bricks". The modules can have one size or different sizes.

The display unit can be connected to one multi-parameter patient monitoring device rack. The display unit can also be connected to a plurality of multi-parameter patient monitoring device racks, for example, when the number of parameters that require simultaneous monitoring exceeds the module hosting capacity of one device rack.

The present disclosure also provides a solution to the technical problem of lack of compatibility between small portable patient monitoring devices and the docking stations of a multi-parameter patient monitoring system. A dual-use patient monitor module can function as a stand-alone device with its own sensor(s), processing unit, and display screen. When used as a stand-alone device, the module can have a handle in an extended position to improve transportability. The dual-use patient monitor module can also be fit into a dock on a multi-parameter patient monitoring device rack when a handle on the dual-use device is folded down. The dual-use device housing can have a recess or groove configured to house the folded-down handle so that the housing can have a smooth outer profile.

A multi-parameter patient monitoring system of the present disclosure can comprise a device rack including a plurality of docks, wherein the plurality of docks can be configured to receive a plurality of patient monitor modules, the plurality of patient monitor modules each configured for connecting to one or more sensors so as to measure one or more physiological parameters, the device rack further comprising a signal processing unit configured to receive and process signals from the patient monitor modules; and a display unit physically separate from the device rack and having a separate housing and configured to communicate with the signal processing unit of the device rack to display values of the one or more physiological parameters determined by the signal processing unit, the display unit further comprising a graphics processing unit. The graphics processing unit can comprise a housing, the housing comprising a plurality of vent openings. The graphics processing unit can comprise an outer shell, the housing disposed at least partially within the shell so that liquid drops onto the graphics processing unit are directed away from the vent openings by the shell. An inner surface of the shell can be spaced apart from the vent openings by a gap of a predetermined size. The graphic processing unit can be generally rectangular, the inner surface of the shell being spaced apart from an outer side surface of the housing by a gap on all four sides. The shell can comprise an opening that allows access to cable connection ports on the housing, the opening on a side of the housing with no vent openings. The shell can comprise an opening, the opening allowing access to a mounting arm connector on a front surface of the housing. The signal processing unit can be located in a first portion of the device rack and the plurality of docks can be located in a second portion of the device rack, wherein the device rack can comprise a first vent opening in the first portion. The device rack can further comprise a second vent opening in the second portion so that a fan in the second portion can draw air into the second portion, wherein the air can flow over the signal processing unit and exits through the first vent opening. The system can further comprise a second device rack including a plurality of docks and a signal processing unit, the second device rack in electrical communication with the display unit so as to display values of additional physiological parameters on the display unit. Each of the plurality of docks can be uniformly sized, and the plurality of docks can be configured to receive modular patient monitor modules having a size configured to fit into one or more of the uniformly sized docks.

A method of measuring and displaying a value of a physiological parameter using a multi-parameter patient monitoring system can comprise using a signal processing unit, receiving a patient data signal from a patient monitor processing module received in a dock of a device rack of the multi-parameter patient monitoring system, the device rack comprising a housing that encloses the signal processing unit and at least a portion of the dock; processing the patient data signal so as to determine one or more physiological parameters of a patient; and providing the determined one or more physiological parameters to a graphics processing unit located in a separate housing, wherein the separate housing can be attached to a display unit. The method can further comprise using the graphics processing unit, receiving the determined one or more physiological parameters from the signal processing unit; and rendering display content related to the determined one or more physiological parameters for the display unit. The method can further comprise activating a fan inside the device rack housing to cool the signal processing unit. The device rack housing can comprise at least two vent openings on opposite sides of the housing, the fan configured to draw air across the at least two vent openings. The method can further comprise activating a fan inside the separate housing to cool the graphics processing unit. The separate housing can comprise at least two vent openings on opposite sides of the separate housing, the fan configured to draw air across the at least two vent openings. The method can further comprise using a second signal processing unit of a second device rack to receive and process a second patient data signal from a second patient monitor module received in the second device rack so as to determine additional physiological parameters of the patient, and to provide the determined additional physiological parameters to the graphics processing unit.

A device rack of a multi-parameter patient monitoring system can have improved heat dissipation. The device rack can be configured to electrically communicate with a graphics processing unit outside the device rack. The device rack can comprise a device rack housing having a front side, a back side, and a side surface extending between the front and back sides, the back side comprising a plurality of vent openings; a dock housing comprising a plurality of docks configured to receive a plurality of patient monitor modules, the plurality of patient monitor modules each configured for connecting to one or more sensors so as to measure one or more physiological parameters, wherein the dock housing can be located in a first portion of the device rack housing and can be spaced apart from an inner wall of the device rack housing to define a gap; a signal processing unit configured to receive and process signals from the patient monitor modules, wherein the signal processing unit can be located in a second portion of the housing; and a fan located in the second portion of the housing and at or near the plurality of openings on the back side, wherein the fan can be configured to draw air into the gap to flow past the signal processing unit before exiting through the plurality of vent openings. The dock housing can comprise a plurality of vent openings adjacent to the gap. The gap can be located in a recessed or inclined portion of the housing. The dock housing can extend outward from the front side of the device rack.

A stand-alone graphics processing unit of a multi-parameter patient monitoring system with improved heat dissipation can comprise a housing comprising a front surface, a back surface, and a side surface extending between the front and back surfaces to define a substantially enclosed space, the housing comprising a plurality of vent opening on opposite sides of the side surface; one or more graphics processors in the enclosed space, the one or more graphics processors configured to communicate with a signal processing unit of the multi-parameter patient monitoring system to receive values of the one or more physiological parameters determined by the signal processing unit, the signal processing unit located in a device rack of the multi-parameter patient monitoring system; and a fan in the enclosed housing, wherein the fan can be configured to draw air across the plurality of vent openings on the opposite sides of the side surface so as to cool the graphics processors. The unit can further comprise an outer shell extending around the side surface of the housing so that liquid drops onto the unit can be directed away from the vent opening by the shell. An inner surface of the shell can be spaced from the vent opening on the housing by a gap of a predetermined size, the gap allowing air to enter and/or exit through the plurality of vent openings. The front surface of the housing can extend outward from the outer shell.

A hardware processing unit of the present disclosure for use in an environment in which the hardware processing unit is exposed to fluid drops can comprise one or more hardware processors; a housing comprising a front surface, a back surface, and a side surface extending between the front and back surfaces to define a substantially enclosed space, the one or more hardware processors disposed in the enclosed space, the side surface of the housing comprising at least one vent opening to allow heat inside the substantially enclose space to be dissipated; and an outer shell extending around the side surface of the housing so that liquid drops onto the unit can be directed away from the at least one vent opening by the shell. An inner surface of the shell can be spaced from the at least one vent opening on the housing by a gap of a predetermined size. The hardware processing unit can be generally rectangular, the inner surface of the shell being spaced apart from the side surface of the housing by a gap on all four sides. The front surface of the housing can extend outward from the outer shell. The hardware processing unit can further comprise a fan in the substantially enclosed space of the housing, wherein the housing can comprise at least two vent openings on opposite sides of the housing, the fan configured to draw air across the at least two vent openings. The shell can comprise one or more openings that allow access to electrical and/or mechanical connectors on the housing.

A hardware processing unit for use in an environment in which the hardware processing unit is exposed to fluid drops can comprise one or more hardware processors; a housing comprising a front side, a back side, and a side surface extending between the front and back sides, the one or more hardware processors disposed in the housing, the housing comprising at least one vent opening on each of two opposite sides of the housing to allow heat inside the housing to be dissipated; and an outer shell extending around the side surface of the housing so that liquid drops onto the unit can be directed away from the vent openings by the shell. The housing can extend outward from the outer shell at the front or back side of the housing. The unit can further comprise a fan to draw air across the at least one vent opening on one of the two opposite sides to the at least one vent opening on the other of the two opposite sides. A substantially enclosed space can be defined by the side surface extending between the front and back sides of the housing, the vent openings located on opposite sides of the side surface. The vent openings can be located on the front and back sides of the housing. The vent opening on the front side of the housing can be located at a recessed or inclined portion of the housing.

A dual-use patient monitoring device of the present disclosure can comprise a plurality of ports configured for connecting to one or more sensors; a processing unit in communication with the one or more sensors and configured to measure one or more patient parameters; a display unit in communication with the processing unit and configured to display the one or more patient parameters; and a housing with a foldable handle, wherein the handle can have a retracted position to allow the housing to be docked into a multi-parameter patient monitoring device rack having a plurality of docks, and wherein the handle can have an extended position to allow the device to be carried by holding onto the handle. The housing can comprise a recess, the recessed configured to receive the handle in the retracted position so that the handle does not protrude outward from an outer wall of the handle. The housing can be generally rectangularly shaped. The handle can be located at a surface that faces upward when the device is placed in an upright position.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. Corresponding numerals indicate corresponding parts.

DETAILED DESCRIPTION

Aspects of the disclosure are provided with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit scope of the disclosure herein, which is instead defined by the claims following this description.

The multi-parameter patient monitoring device racks described herein can have the same functionality as the hub described in U.S. patent application Ser. No. 14/512,237, filed Oct. 10, 2014 and entitled "SYSTEM FOR DISPLAYING MEDICAL MONITORING DATA", which is incorporated herein by reference in its entirety, except that the multi-parameter patient monitoring device racks of the present disclosure do not have an integrated display unit. A remote display unit, such as a tablet PC or commercial television, in wireless communication with the multi-parameter patient monitoring device rack, can provide the same functionality as the display device of the hub described in U.S. patent application Ser. No. 14/512,237.

Figure 1A:
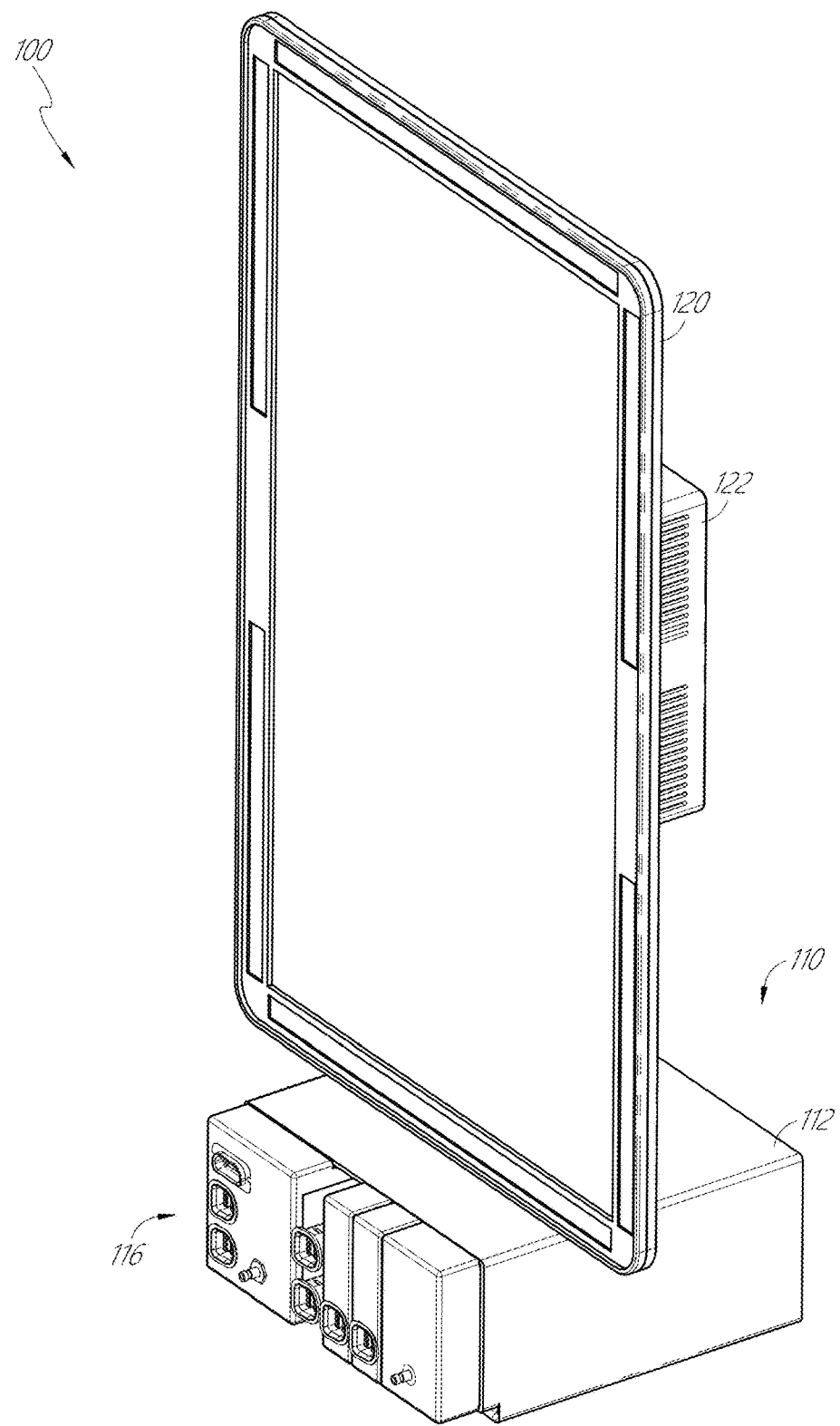
FIGS. 1A-1B illustrate perspective views of an example multi-parameter patient monitoring system having a device rack and a display unit.
Figure 1B:
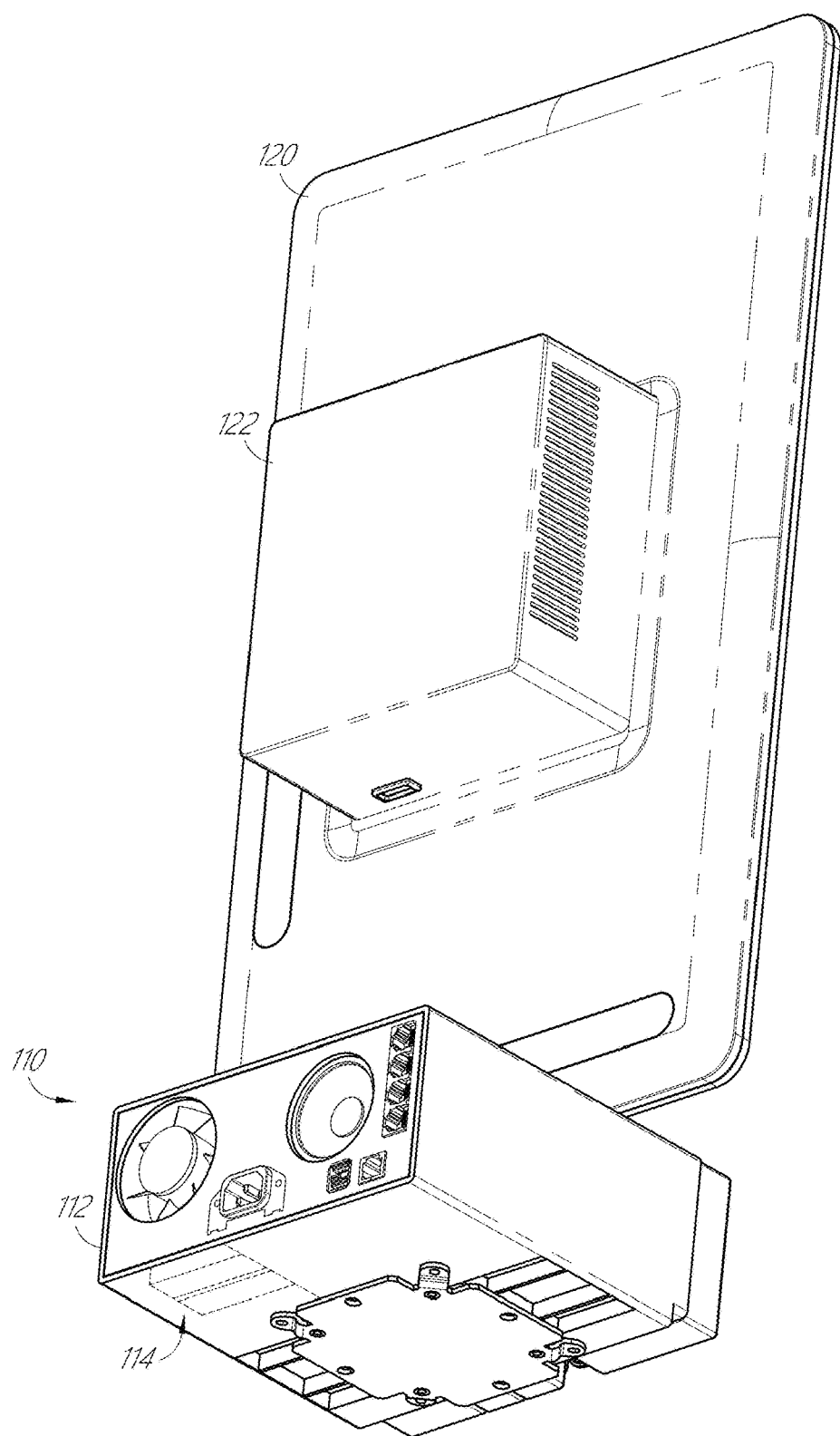

As shown in FIGS. 1A and 1B, a multi-parameter patient monitoring system 100 can have a device rack 110 in communication with a separate display unit 120. The device rack 110 and the display unit 120 can be connected using any known wireless technology. The device rack 110 and the display unit 120 can also be connected with cables. The connection between the multi-parameter patient monitoring device rack and the display unit can be by cables, by wireless technology, or both. The multi-parameter patient monitoring device rack can be in electrical communication with any types of display unit, for example, with a tablet PC, a laptop, a TV, a large screen graphic display screen, and the like. As disclosed herein, the device rack 110 can be in electrical communication with a graphic display unit 120. The graphic display unit 120 can be attached to a graphic processing unit 122.

Figure 1C:
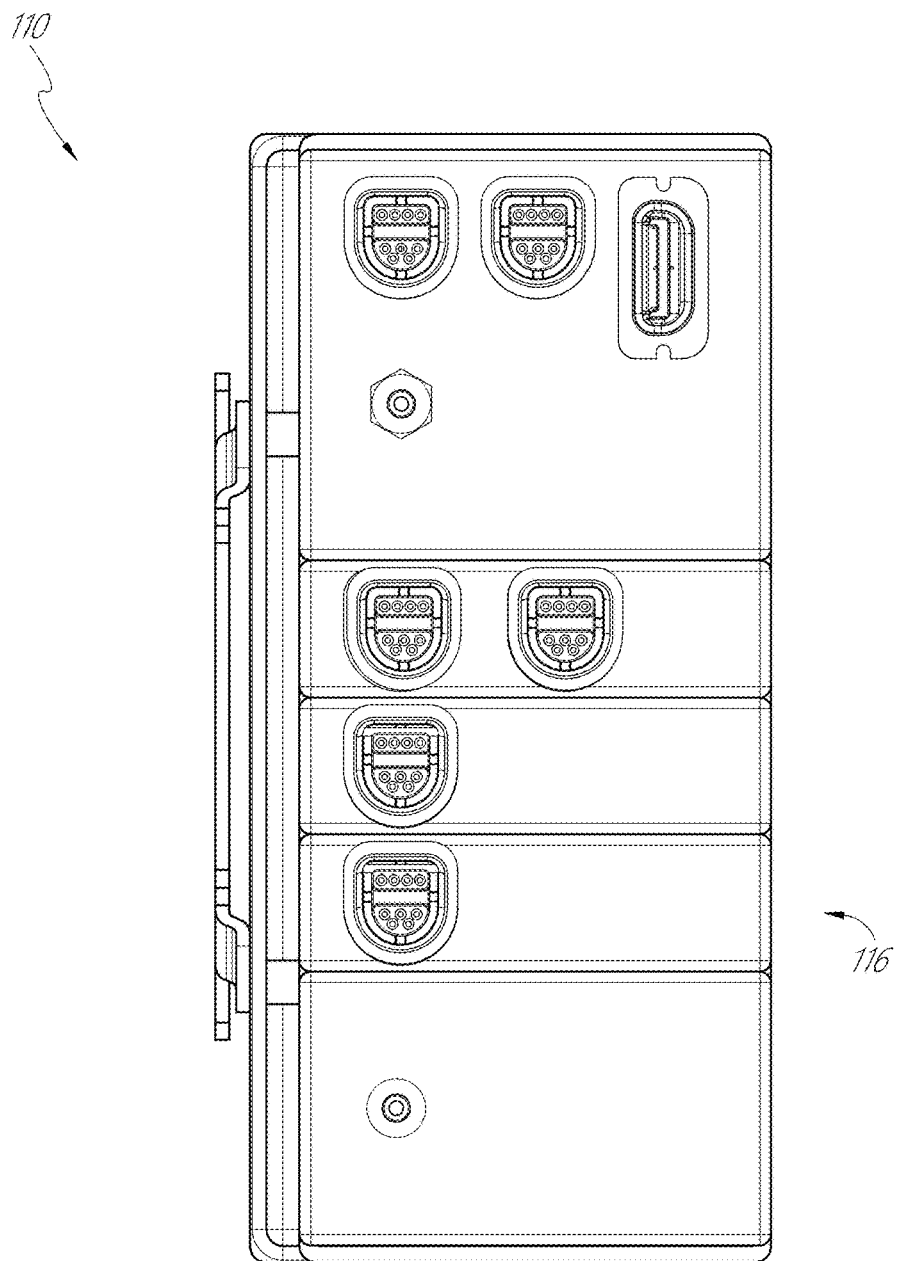
FIGS. 1C-1F illustrate front, back, top, and side views of the device rack of FIGS. 1A-1B with a plurality of patient monitor modules received in the device rack.
Figure 1D:
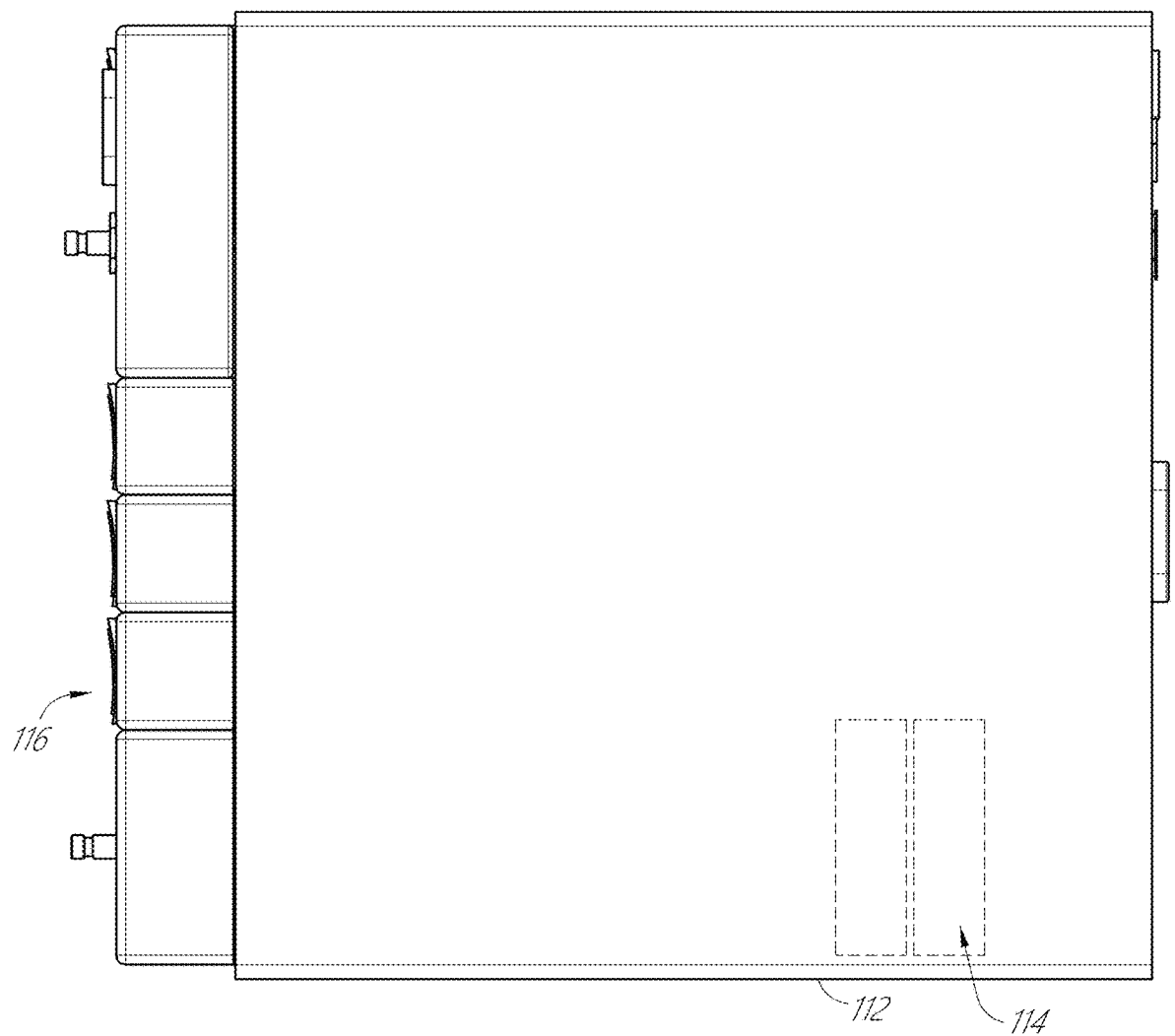
Figure 1E:
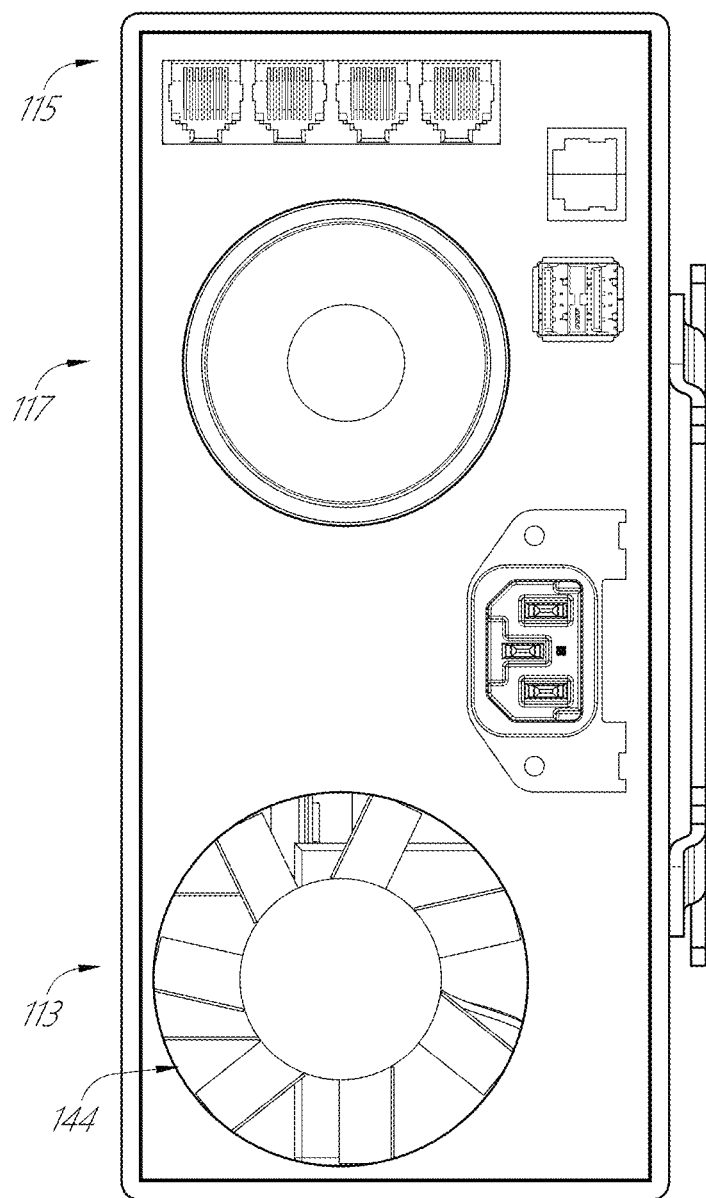
Figure 1F:
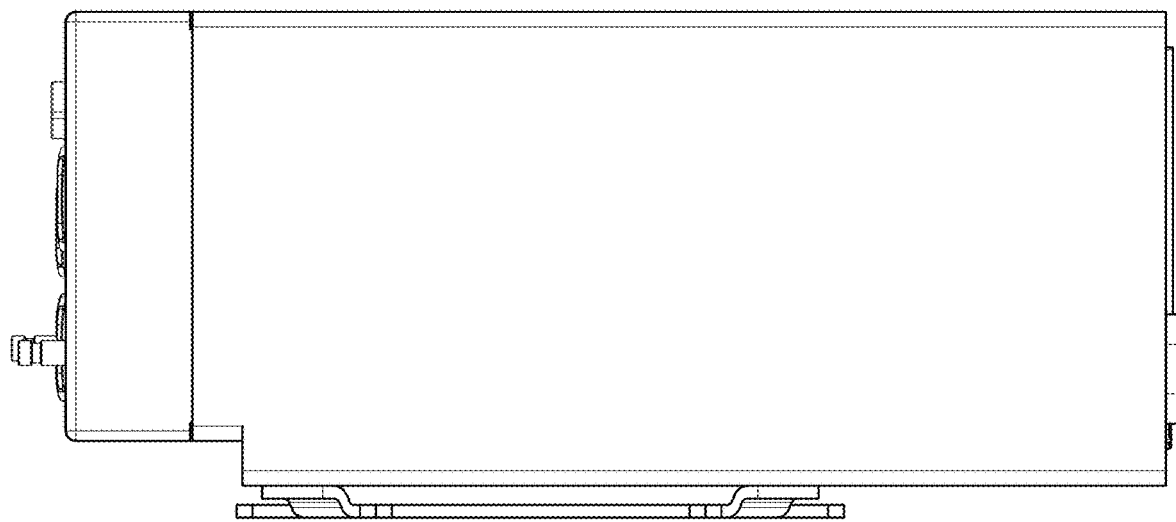
Figure 1G:
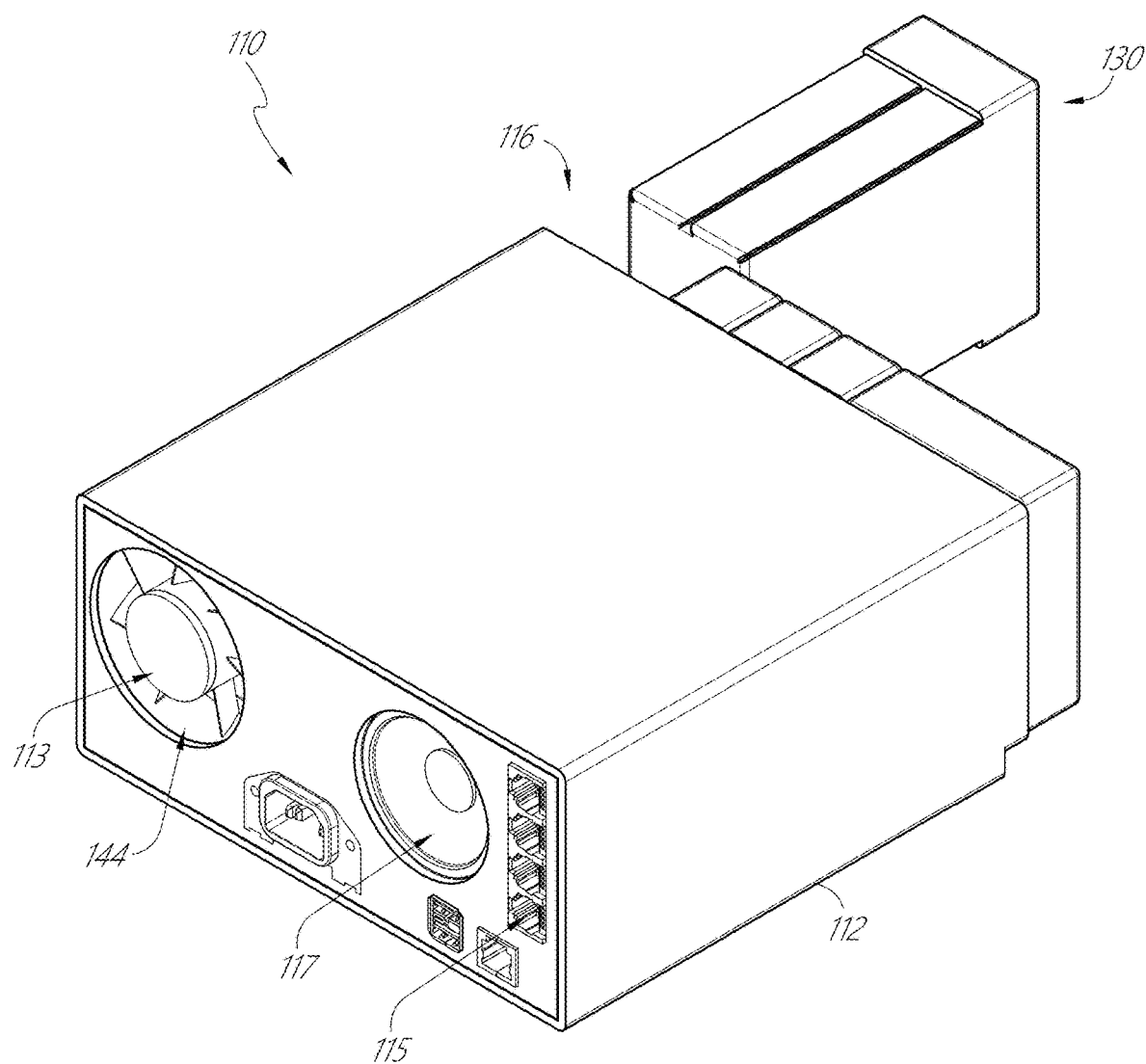
FIGS. 1G and 1H illustrate partially exploded perspective views of the device rack with one patient monitor module removed.

As shown in FIGS. 1C and 1D, the device rack 110 can have a rack housing 112 enclosing a plurality of docking stations 116. The housing 112 can also enclose a signal processing unit 114. As shown in FIGS. 1E and 1G, the device rack 110 can also include a fan 113 on or near its back side. The device rack 110 can further include a plurality of cable ports 115 configured for receiving one or more cables, such as for connecting to the display unit 120, to another device rack, and/or to a power supply. The multi-parameter monitoring device rack can also house a battery. The device rack can further have a speaker 117 for audio output.

Figure 1H:
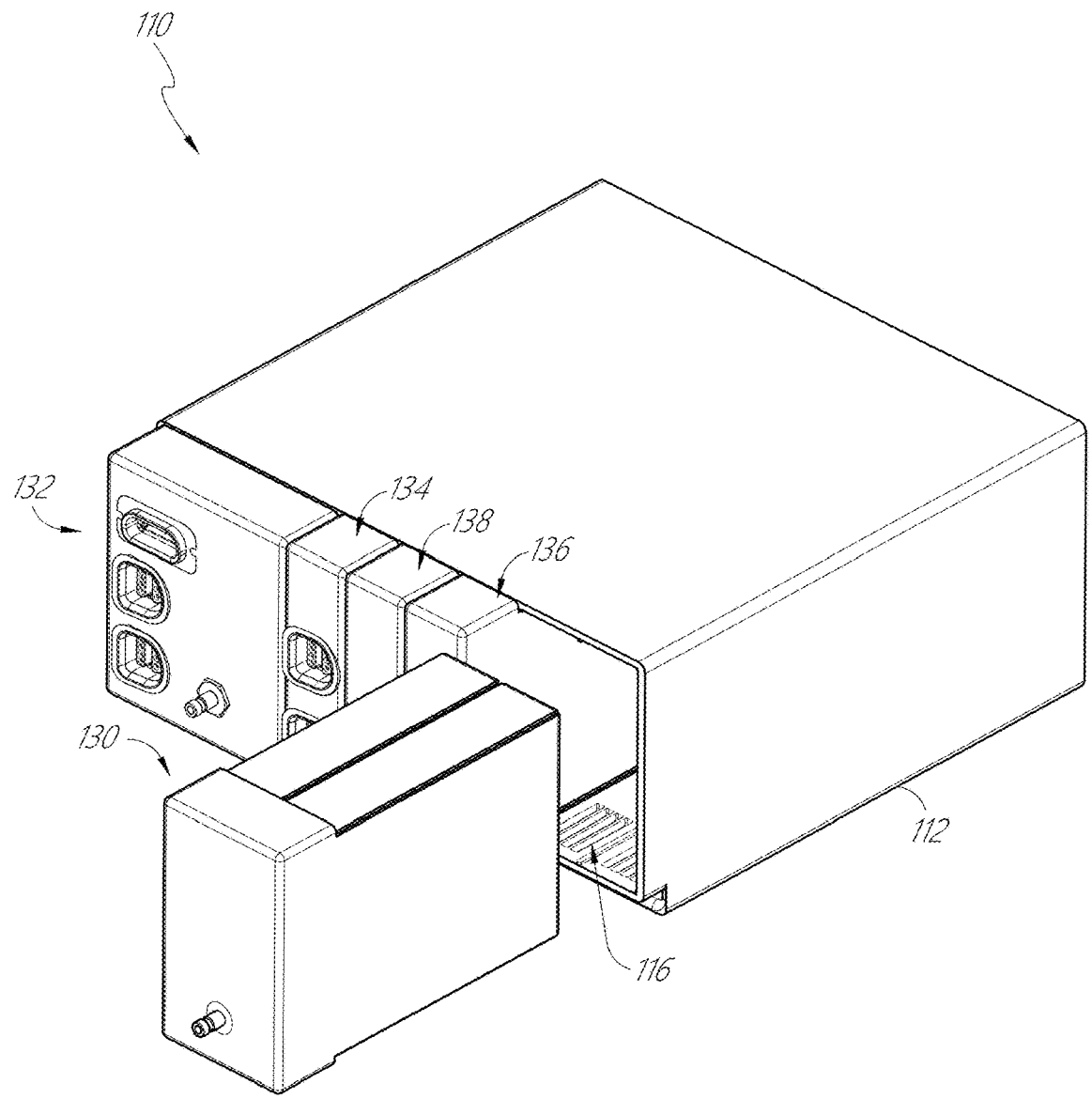

As shown in FIG. 1H, the plurality of docks 116 can receive patient monitor modules or bricks 130, 132, 134, 136, 138. The docks 116 can have varying sizes. The docks 116 can also have the same size. The patient monitor modules 130, 132, 134, 136, 138 can each include one or more sensors ports configured to connect with one or more sensors. The patient monitor modules 130, 132, 134, 136, 138 can also each optionally have a processing unit configured to be in communication with one or more connected sensors to measure any of the parameters described above. The patient monitor modules 130, 132, 134, 136, 138 can each optionally have its own display device to display values of the patient parameters.

When the patient monitor modules 130, 132, 134, 136, 138 are received in the plurality of docks 116, signals from the individual modules 130, 132, 134, 136, 138 can be sent to the signal processing units 114 of the multi-parameter monitoring device rack 110 for processing. The multi-parameter monitoring device rack 110 can in turn output one or more values of physiological parameters to be displayed on the separate display unit 120. Parameters measured by the individual modules can be displayed, for example, simultaneously on the separate display unit. The individual modules 130, 132, 134, 136, 138 can be made by the same manufacturer as the device rack. At least some of the individual modules 130, 132, 134, 136, 138 can also be third-party modules made by different manufacturers.

Figure 2A:
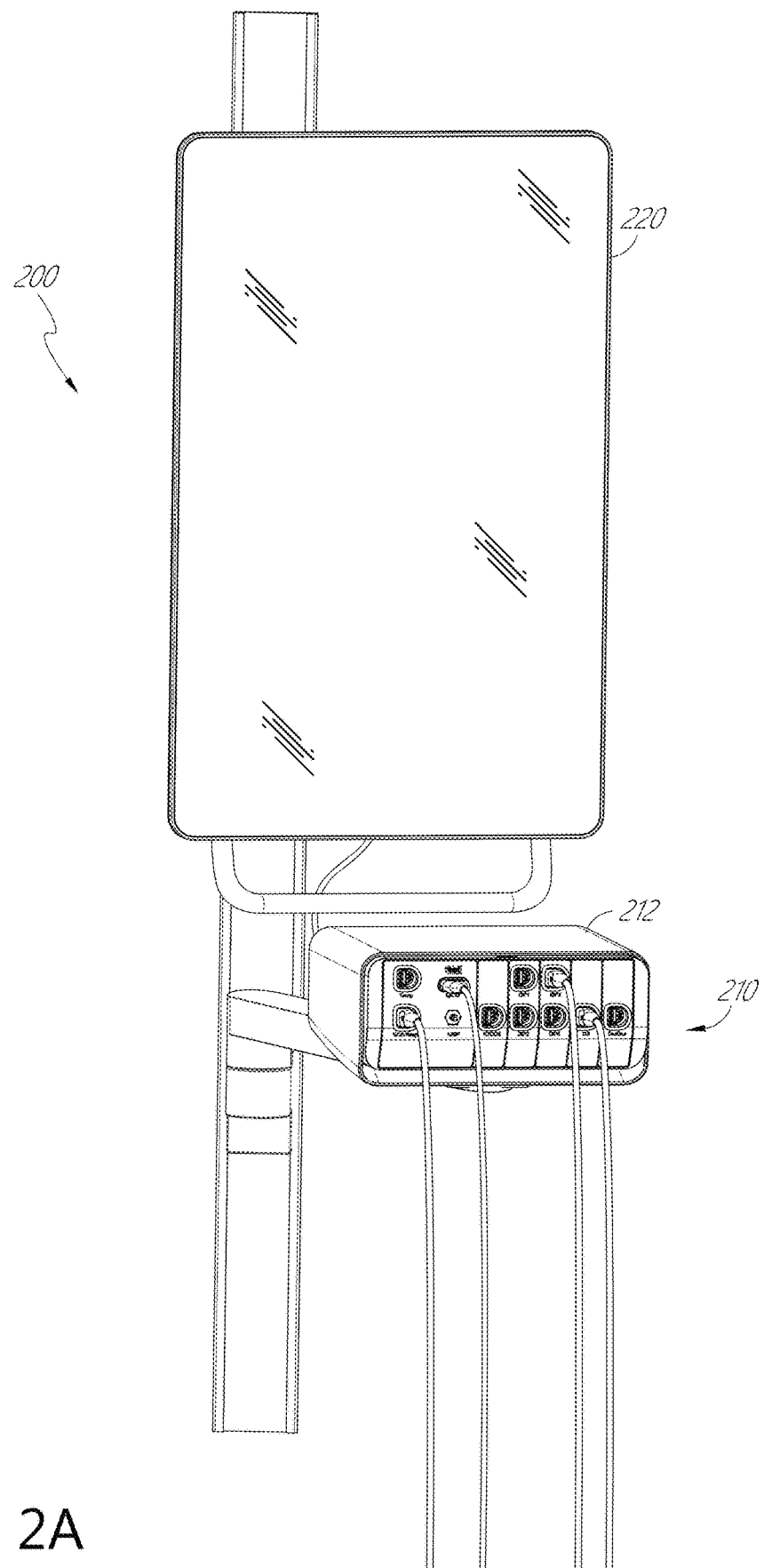
FIGS. 2A-2B illustrate perspective views of another example multi-parameter patient monitoring system.
Figure 2B:
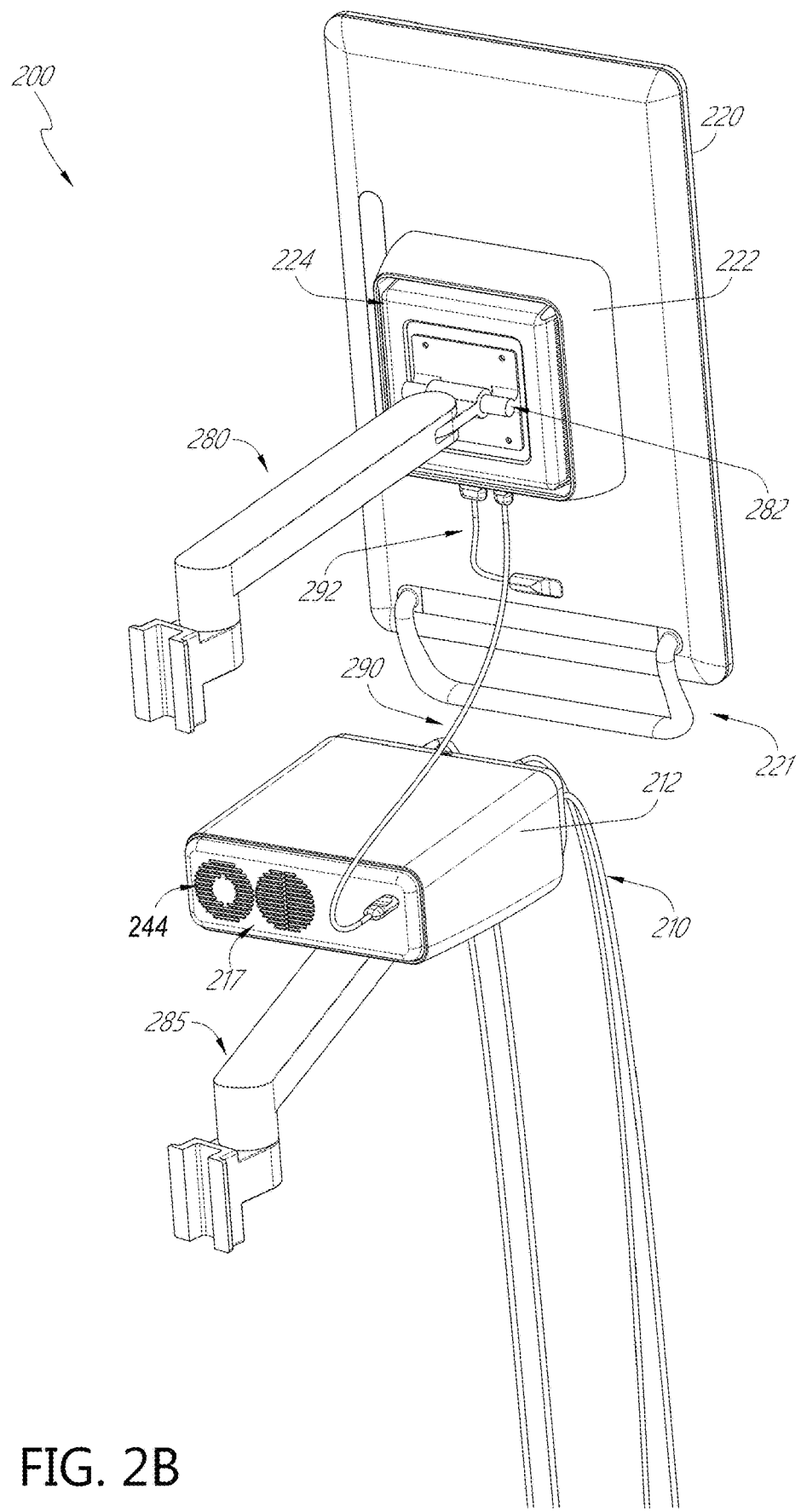

FIGS. 2A and 2B illustrate a multi-parameter patient monitoring system 200 having any of features of the multi-parameter patient monitoring system 100 and other features described below. Accordingly, features of the multi-parameter patient monitoring system 100 can be incorporated into features of the multi-parameter patient monitoring system 200, and features of the multi-parameter patient monitoring system 200 can be incorporated into features of the multi-parameter patient monitoring system 100. Corresponding parts are designated corresponding reference numerals with the same last two digits throughout the disclosure.

The multi-parameter patient monitoring system 200 can have a device rack 210 in communication with a separate display unit 220. The graphic display unit 220 can be attached to a graphics processing unit 222. The graphics processing unit 222 can be attached to a side of the graphic display unit 220 opposite a display screen.

The graphic display unit 220 can be mounted to a movable mounting arm 280. The mounting arm 280 can have one end fixed to a wall or table in a hospital room. The mounting arm 280 can also have the one end fixed to a movable cart. As shown in FIG. 2B, the other end of the mounting arm 280 can be pivotally and/or rotationally coupled to a mounting bar 282 on a housing 224 of the graphics processing unit 222. The housing 224 can have a front side and a back side. The back side can be the side facing the display unit 220. The mounting bar 282 can be located on the front side. The mounting arm 280 can also optionally be coupled to the display unit 220 instead. The coupling of the mounting arm 280 and the graphics processing unit 222 and/or the graphic display unit 220 can be achieved by any coupling features, such as by magnets, ball and socket joint, and the like. The display unit 220 can include one or more handles 221 to improve ease in adjusting a position of the display unit 220. The location of the handle(s) 221 is not limiting. The device rack 220 can be supported by a second mounting arm 285. The mounting arm 280 and the second mounting arm 285 can be fixed to the same reference object, such as to the wall of a hospital room or the same cart, or to different reference objects.

The device rack 210 and the graphics processing unit 222 can be connected with cables 290. The graphics processing unit 222 and the display unit 220 can be connected with a cable 292. The connections described herein can also alternatively or additionally be achieved by wireless technology.

Figure 3A:
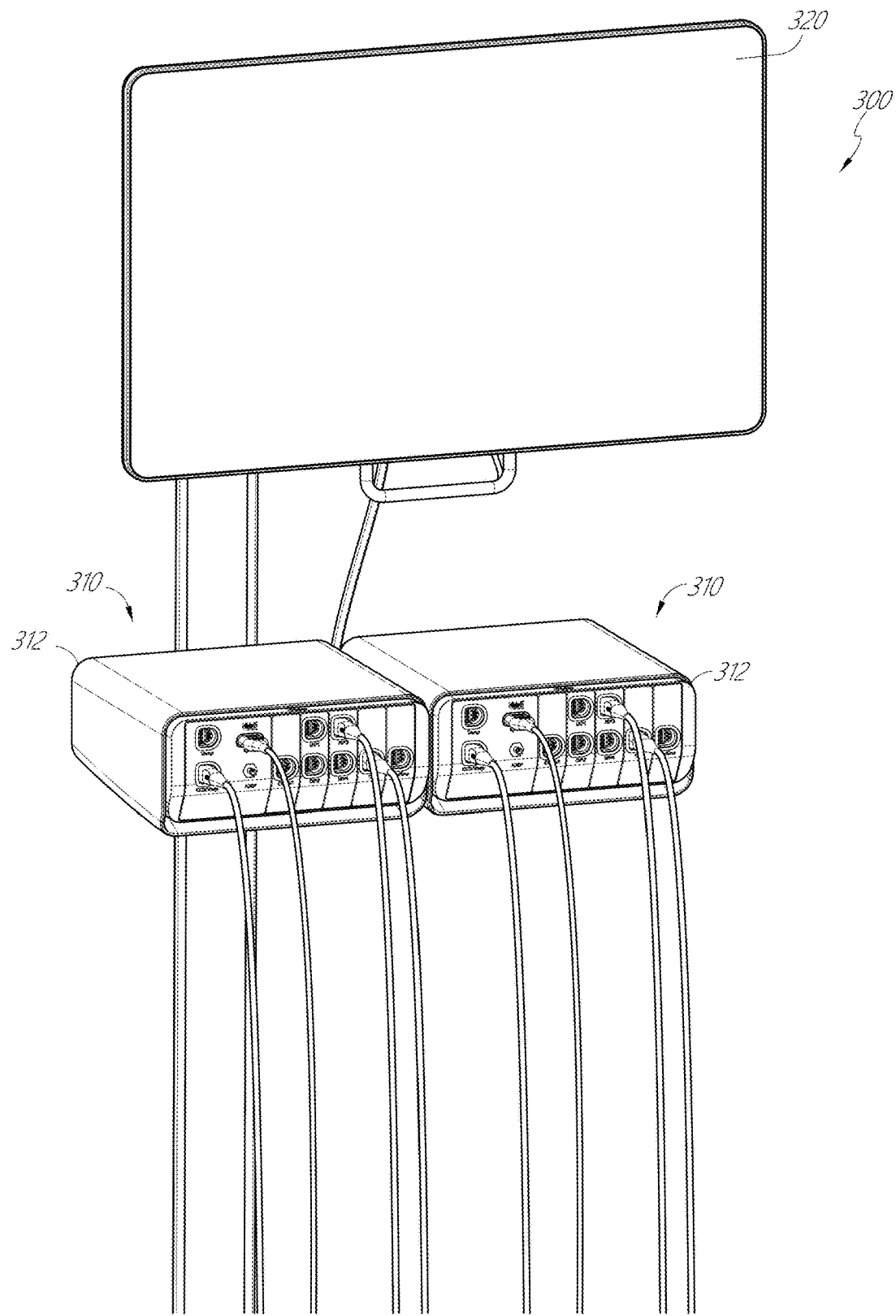
FIGS. 3A-3B illustrate perspective views of another example multi-parameter patient monitoring system.
Figure 3B:
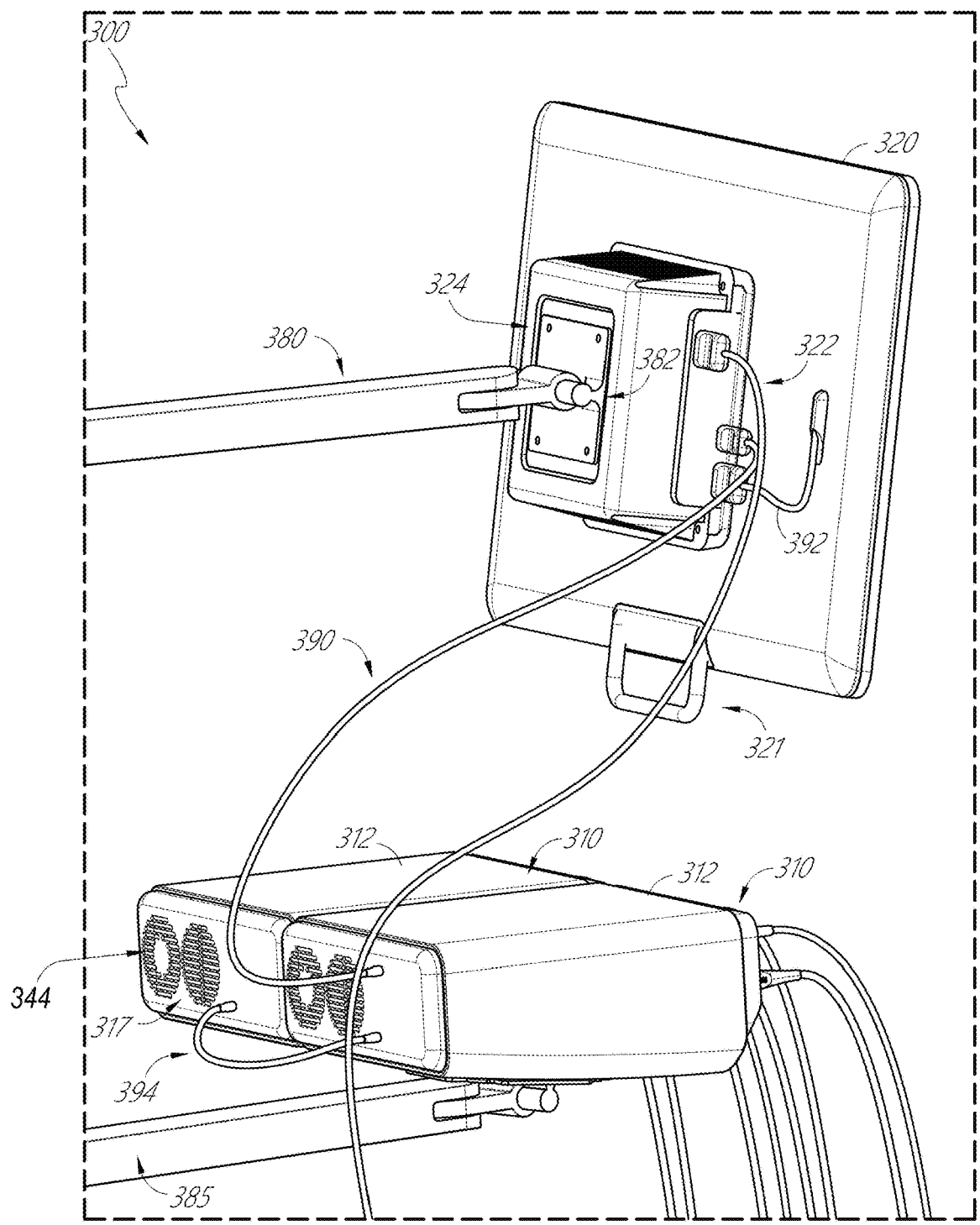

FIGS. 3A and 3B illustrate a multi-parameter patient monitoring system 300 having any of features of the multi-parameter patient monitoring system 100, 200 and other features described below. Accordingly, features of the multi-parameter patient monitoring system 100, 200 can be incorporated into features of the multi-parameter patient monitoring system 300, and features of the multi-parameter patient monitoring system 300 can be incorporated into features of the multi-parameter patient monitoring system 100, 200. Corresponding parts are designated corresponding reference numerals with the same last two digits.

The multi-parameter patient monitoring system 300 can have a first device rack 310 and a second device rack 310 in communication with a separate display unit 320. The graphic display unit 320 can have a greater display area than the display unit 120, 220, to display more parameters from the first and second display racks 310.

The graphic display unit 320 can be attached to a graphics processing unit 322. The graphics processing unit 322 can be attached to a side of the graphic display unit 320 opposite the display screen. The graphic display unit 320 can be mounted to a movable mounting arm 380 as described above. As shown in FIG. 3B, the mounting arm 380 can be pivotally and/or rotationally coupled to a mounting bar 382 on a housing 324 of the graphics processing unit 322. The type of coupling of the mounting arm 380 and the graphics processing unit 322 and/or the graphic display unit 320 is not limiting. The display unit 320 can include one or more handles 321 to improve ease in adjusting a position of the display unit. The location of the handle(s) 221 is not limiting. The device racks 310 can also be supported by a second mounting arm 385.

The device racks 310 and the graphics processing unit 322 can be connected with one or more cables 390. The graphics processing unit 322 and the display unit 322 can be connected with a cable 392. The first and second device racks 310 can also be connected by a cable 394. The connections described herein can also alternatively or additionally be achieved by wireless technology.

Figure 4:
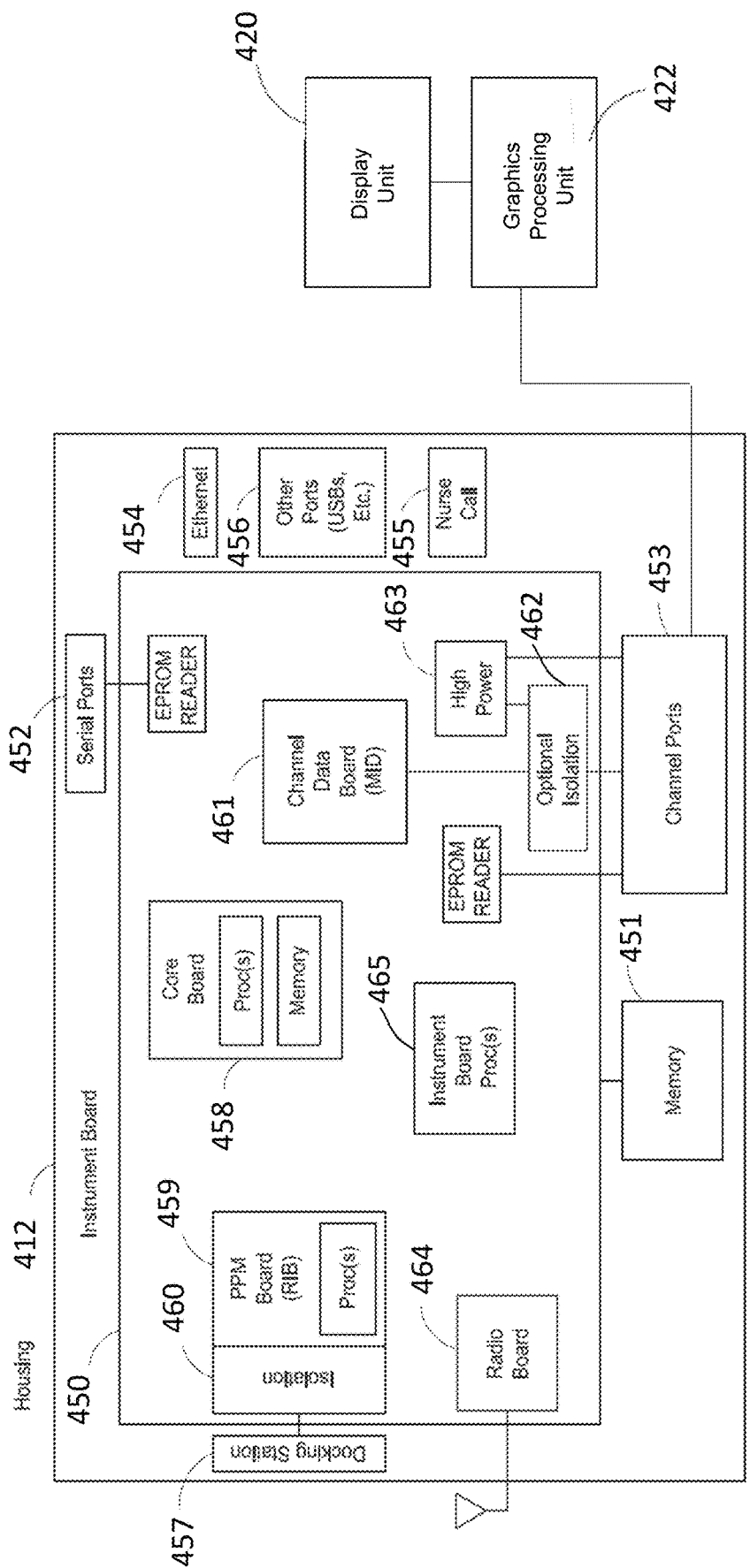
FIG. 4 illustrates an example hardware block diagram of any of the example multi-parameter patient monitoring systems of FIGS. 1A-3B.

FIG. 4 illustrates an example hardware block diagram of the multi-parameter monitoring system as shown in FIGS. 1A-3B. The housing 412 of the device rack can position and/or encompass an instrument board 450 with instrument board processor(s) 465, memory 451, and the various communication connections, which can include the serial ports 452, the channel ports 453, Ethernet ports 454, nurse call port 455, other communication ports 456 including standard USB or the like, and the docking station interface 457.

The instrument board 450 can have one or more substrates including communication interconnects, wiring, ports and the like to enable the communications and functions described herein, including inter-board communications. The instrument board 450 can include a core board 458, which can include the signal processor(s) and other processor(s), and memory. The instrument board 450 can include a portable monitor board ("RIB") 459 with one or more processors and patient electrical isolation 460 for the patient monitor modules. The instrument board 450 can include a channel board ("MID") 461 that can control communication with the channel ports 453, which can include optional patient electrical isolation 462 and power supply 463. The instrument board 450 can include a radio board 464, which can have components configured for wireless communications. Additionally, the instrument board 450 can include one or more processors and controllers, busses, all manner of communication connectivity and electronics, memory, memory readers including EPROM readers, and other electronics recognizable to an artisan from the disclosure herein. Each board can include substrates for positioning and support, interconnect for communications, electronic components including controllers, logic devices, hardware/software combinations and the like. The instrument board 450 can include a large number of electronic components organized in a large number of ways.

The signal processors in the housing 412 of the device rack can output measured patient data to the channel port 453, which can be connected to a channel port on the graphics processing unit 422. The graphics processing unit 422 can cause at least a portion of the patient data to be displayed on the display unit 420. The graphics processing unit 422 can render images, animations, and/or video for the screen of the display unit 420.

As the multi-parameter monitoring device rack 110, 210, 310, 410 and the display unit 120, 220, 320, 420 are separate units, the multi-parameter monitoring device rack and/or the display unit can be highly portable. The display unit may not need to be moved with the multi-parameter patient monitoring device rack and can stay in each room in the hospital. For example, the display unit can be mounted on a wall in the room or on a mounting arm as described above. When multi-parameter patient monitoring is required, one or more multi-parameter monitoring device racks can be brought into the room and connected to the display unit. The multi-parameter patient monitoring device rack can also be mounted on a wall in the room or on a mounting arm as described above.

Compared to having the signal processing unit and the graphics processing unit in the same housing, the multi-parameter patient monitoring systems in FIGS. 1A-4 can have better heat management. Heat generated by the signal processing unit and the graphics processing unit can be dissipated independently of each other through vent openings on the device rack housing and the graphics display unit housing (which will be described below), respectively. The signal processing unit would less likely be overheated due to heat generated by the graphics processing unit and vice versa. Heat dissipation features in the multi-parameter monitoring device racks and the graphics processing unit will be described below.

Example Graphics Processing Units with Improved Heat Dissipation

Figure 5A:
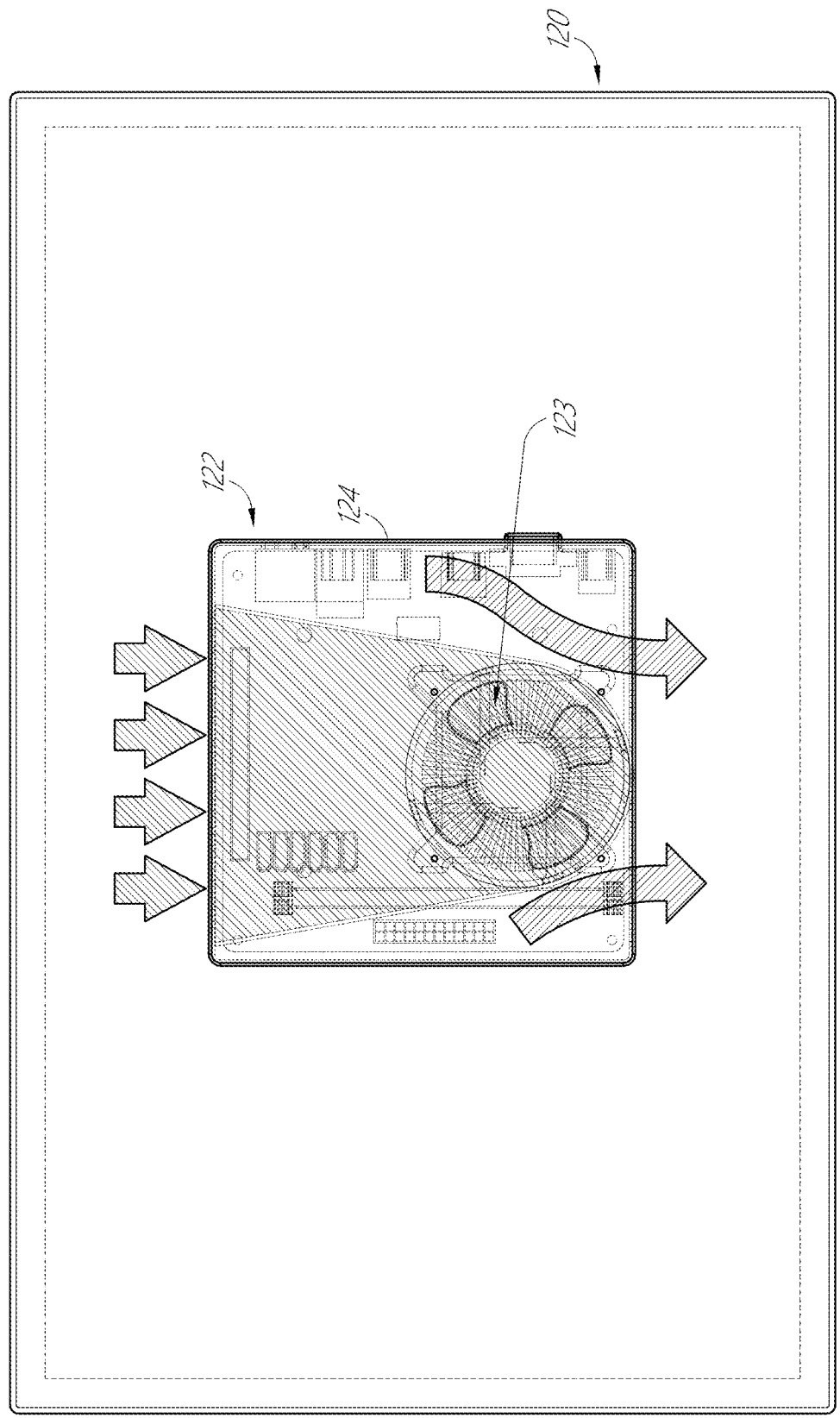
FIGS. 5A-5C illustrate example heat dissipation features of a graphics processing unit attached to a display device of the patient monitoring system of FIGS. 1A and 1B.
Figure 5B:
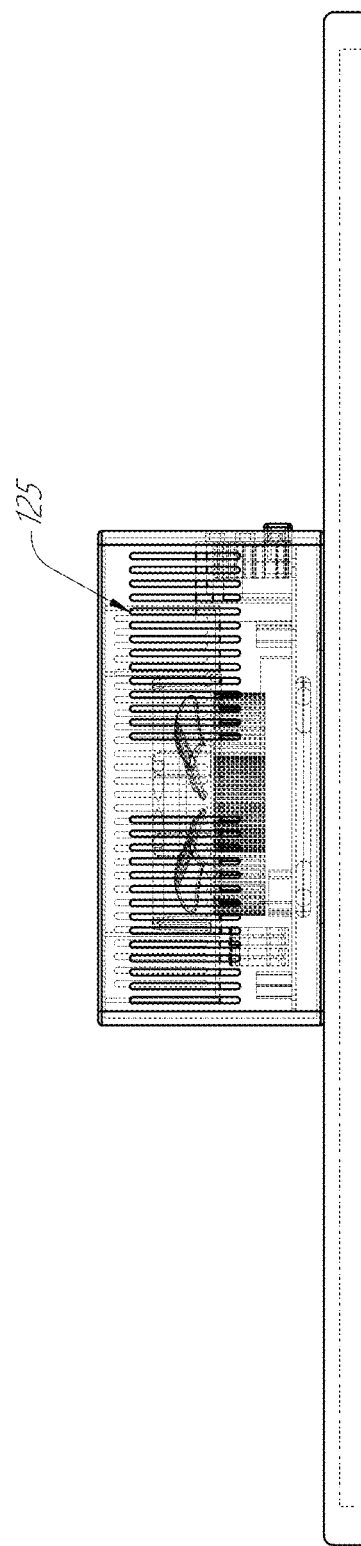
Figure 5C:
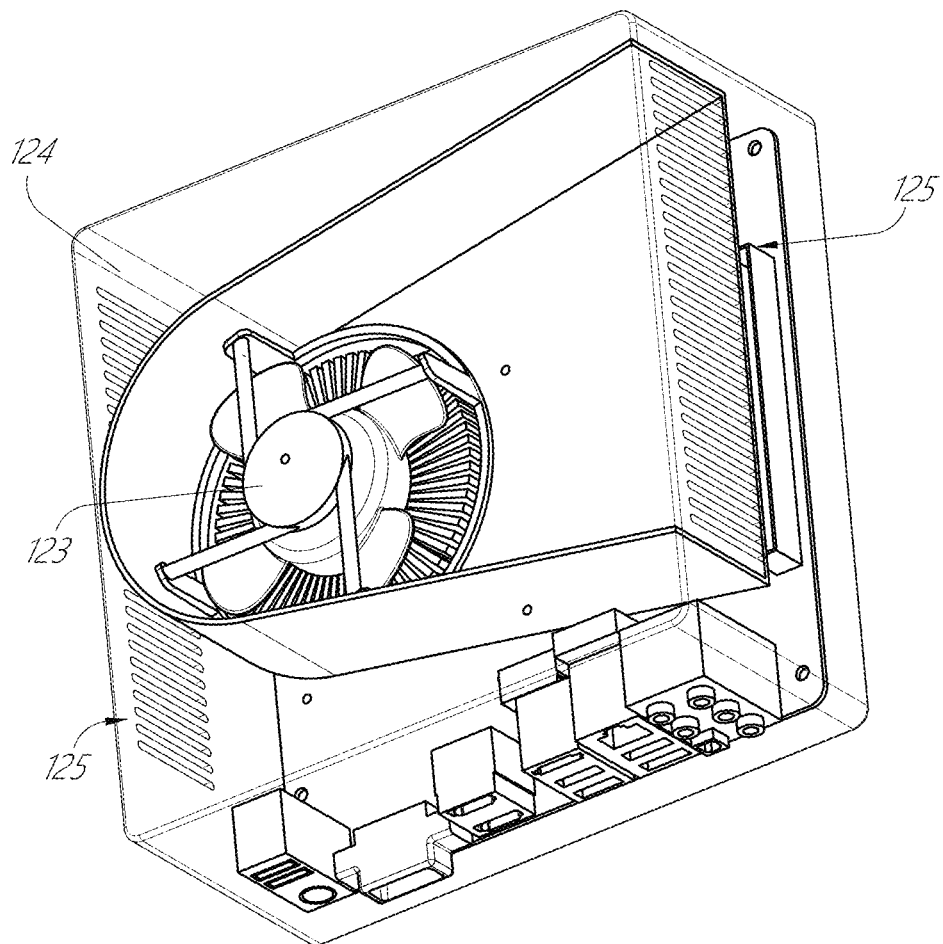

FIGS. 5A-5C illustrate how heat can be dissipated in the graphics processing unit 122 that is coupled to the display unit 120 of the patient monitoring system 100 in FIGS. 1A and 1B. As discussed above, the graphics processing unit can generate heat when in use. As shown in FIGS. 5A-5C, the graphics processing unit 122 can include a fan 123 inside the housing 124. The housing 124 can also include a plurality of vent opening 125 on opposing side walls of the housing 124.

When the fan 123 is turned on, for example, by a controller in the graphics processing unit 122, the vent openings 125 on opposite side walls of the housing 124 can result in a flow of air between the two side walls of the housing 124. Cross flow of air is more efficient at cooling the processors than heat exchanges between air inside and outside the housing via vent openings on only one side of the housing. In FIG. 5A, incoming arrows show cool air, such as air at ambient and/or room temperature, entering the graphics processing unit 122. Outgoing arrows show heated air, such as air having passed over the processors, leaving the graphics processing unit 122. FIG. 5C illustrates the orientation of the graphics processing unit 122 when it is in use. As shown in FIG. 5C, the vent openings 125 can be located on left and right side walls of the housing 124. Having the vent openings 125 on the left and right side walls instead of the top and bottom side walls can reduce the likelihood of liquid drops, such as medication, IV fluids, and the like, from entering into the housing 124.

FIGS. 6A-6G illustrate a graphics processing unit 622, which can be the graphics processing unit 222, 322 of the patient monitoring systems 200, 300 in FIGS. 2A-3B. The graphics processing unit 622 can have any of feature of the graphics processing unit 122 described above and other features described below. Accordingly, features of the graphics processing unit 622 and features of the graphics processing unit 122 can be incorporated into each other.

The graphics processing unit 622 can have a housing 624. The housing 624 has a front surface, a back surface, and a side surface extending between the front and back surfaces to define a substantially enclosed space. The back surface can be facing the display unit 620 when the graphics processing unit 622 is attached to the display unit 620. The front surface can include a mounting bar 682 for coupling with a mounting arm. The graphics processor(s) can be located in the substantially enclosed space. A fan, such as one shown in FIG. 5C, can also be located in the substantially enclosed space. The housing 624 can have a plurality of vent openings 625 (see FIGS. 6E and 6F) on opposite side walls of the housing 624. When the fan is turned on, air can be drawn into the housing 624 via the vent openings 625 on one side and exit the vent opening 625 on the opposite side. As illustrated in FIG. 6E, the vent opening 625 can include a plurality of slits that are substantially parallel to one another on a side wall of the housing 624. The slits can span a substantial portion of a length of the housing 624. The slits can also have a height extending along a substantial portion of a height of the housing 624. As shown in FIG. 6F, each of the openings 625 on one side wall of the housing 624 can face a corresponding opening 625 on the opposite side of the housing 624 so that air can be drawn into one of the vent openings 625 on one side and exit the corresponding vent opening 625 on the opposite side in a straight path. The vent openings 625 can be on the left and right side walls of the housing 624 to reduce the likelihood of liquid drops entering in the housing 624 via the openings 625 than vent openings on top and bottom side walls.

The graphics processing unit 622 can also have an outer shell 626 that can further reduce the likelihood of liquid drops entering through the opening 625. The outer shell 626 can extend at least circumferentially around the side wall of the housing 624. The outer shell 626 can leave the mounting bar 682 exposed for coupling with a mounting arm. The outer shell 626 can be shaped and sized such that when coupled to the housing 626, an inner surface of the shell 626 is spaced apart at least from the vent openings 625 by a gap 640 having a predetermined size. The inner surface of the shell 626 can be spaced apart from the side walls of the housing 624 by a gap 640 around the entire side wall of the housing 624.

Figure 6A:
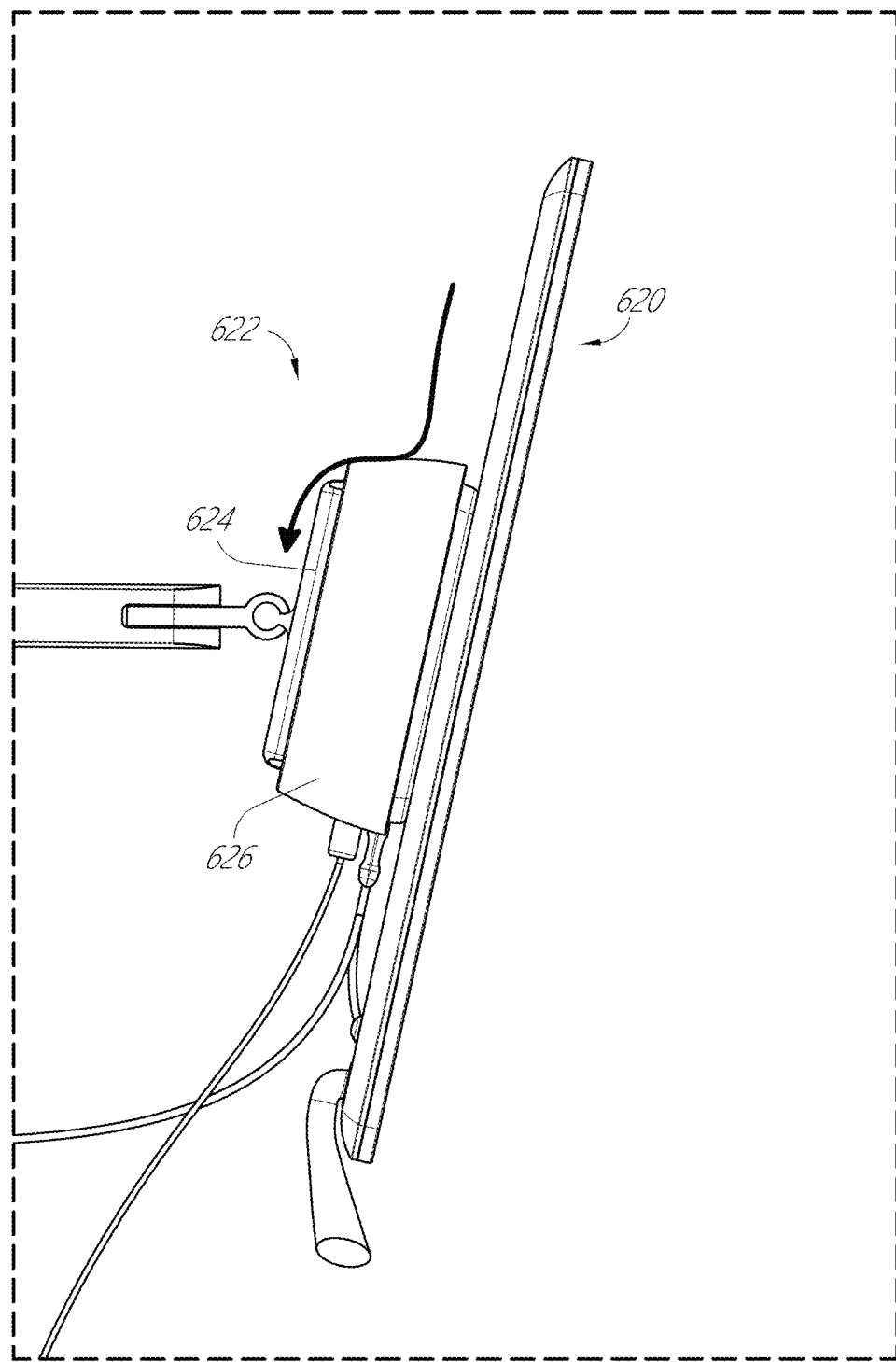
FIGS. 6A-6C illustrate example heat dissipation and drip-proof features of a graphics processing unit attached to a display device of the patient monitoring systems of FIGS. 2A-2B and 3A-3B.
Figure 6B:
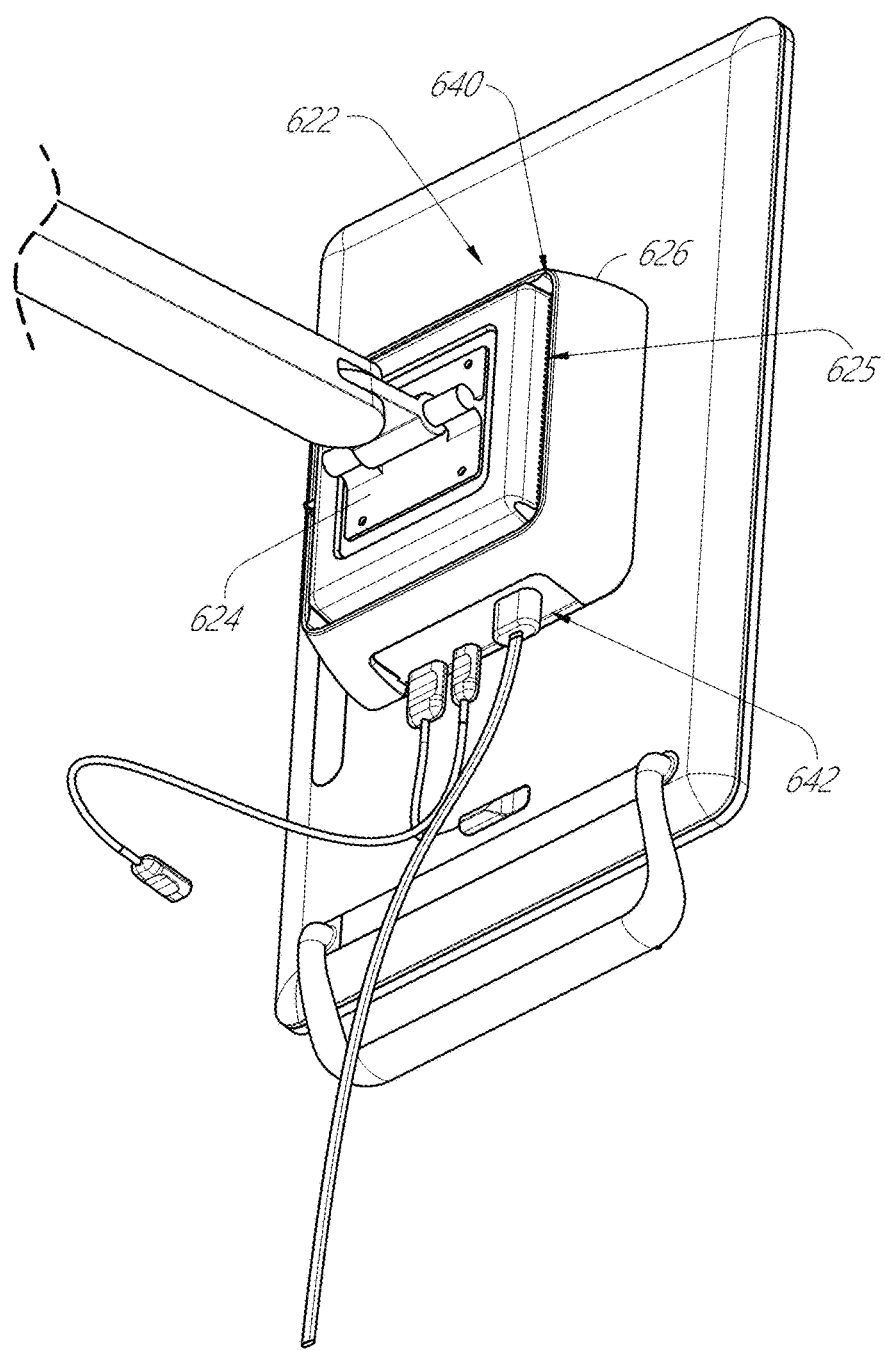
Figure 6C:
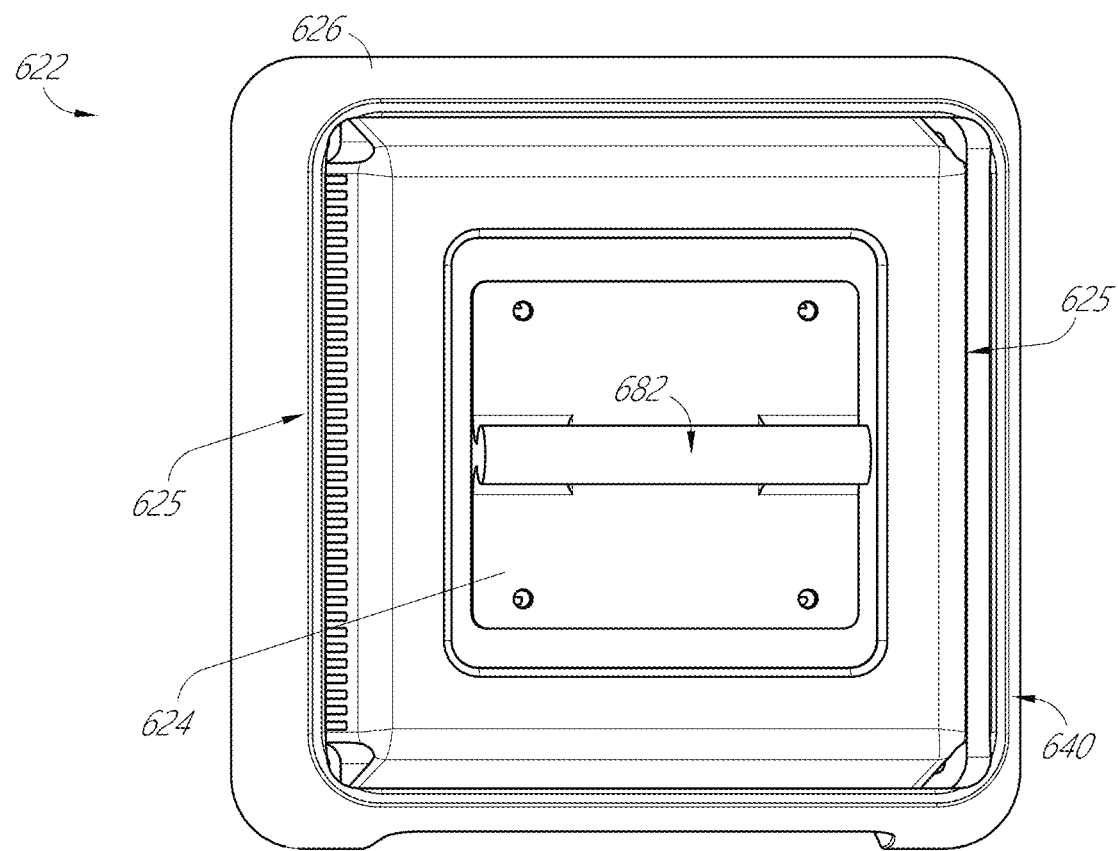
Figure 6D:
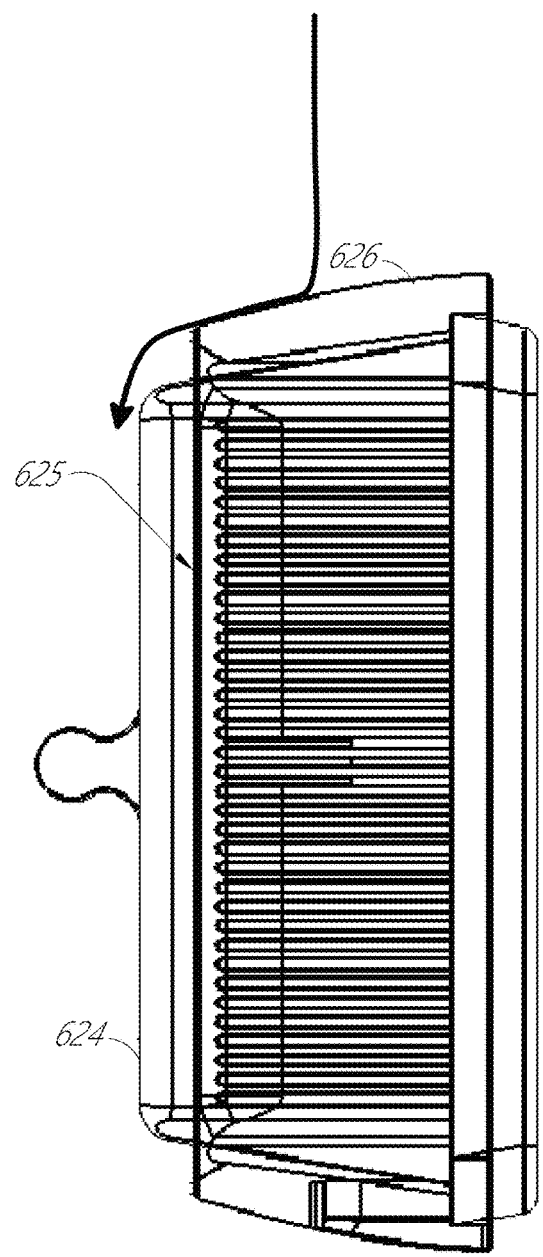
FIG. 6D illustrates an example subassembly of a housing and an outer shell of the graphics processing unit of the patient monitoring systems of FIGS. 2A-2B and 3A-3B.
Figure 6F:
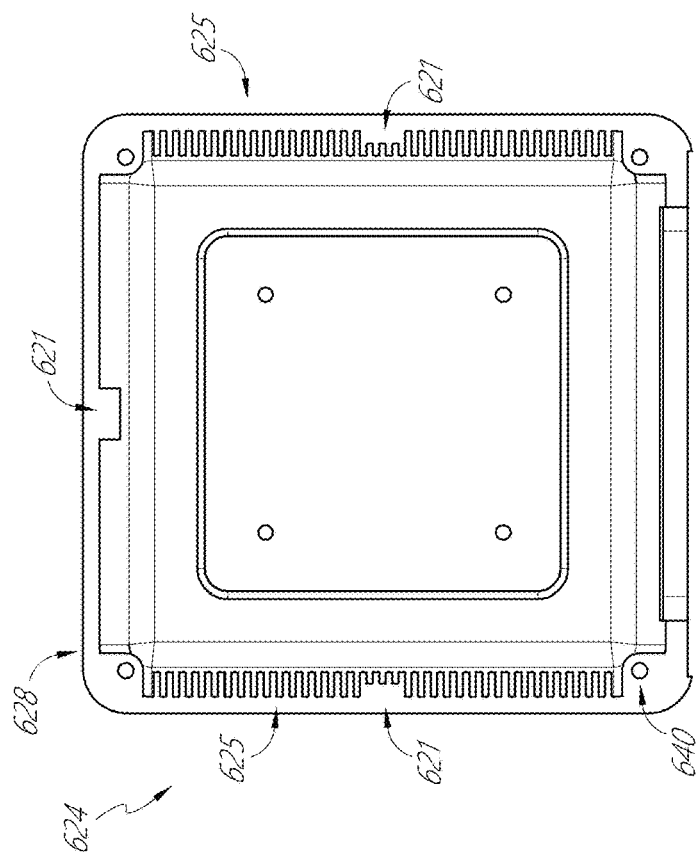
FIGS. 6E-6F illustrate an example housing of the graphics processing unit of the patient monitoring systems of FIGS. 2A-2B and 3A-3B.
Figure 6E:
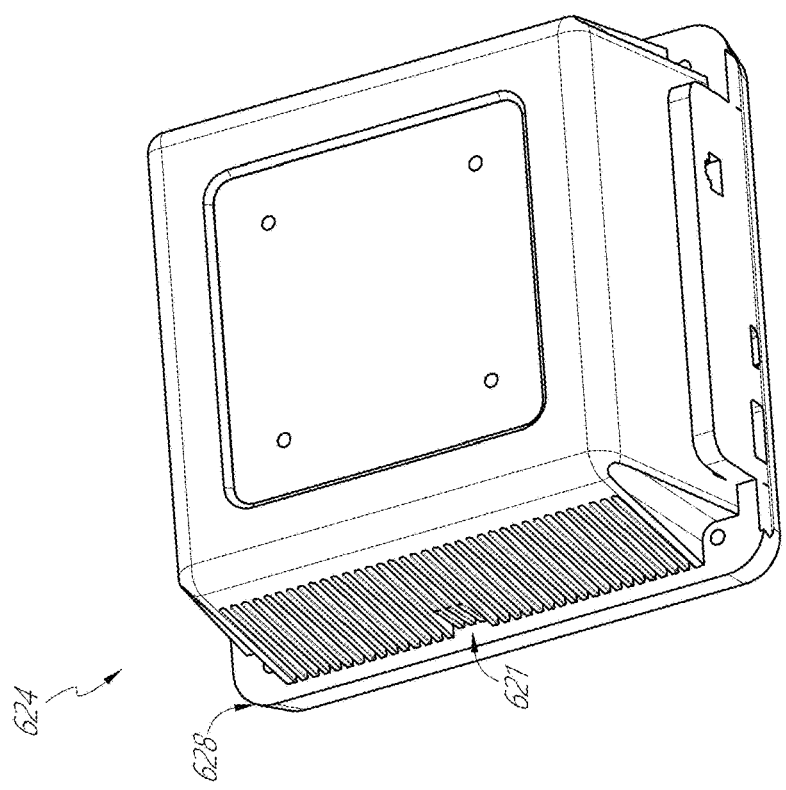

As shown in FIGS. 6A-6C, the graphics processing unit 622 can have a generally rectangular shape, with the housing 624 and the outer shell 626 being also generally rectangular. As shown in FIGS. 6E and 6F, the housing 624 can have one or more grooves 621 on its side walls. The housing 624 can also have a base 628 that has a greater outer dimension (for example, greater width, length, and/or diameter) than a remainder of the housing 624. As shown in FIGS. 6E and 6F, the housing 624 can have one or more fastening holes 641 so that the housing 624 can be attached to the display unit 620 by a plurality of fasteners, such as screws, via the fastening holes 641.

Figure 6G:
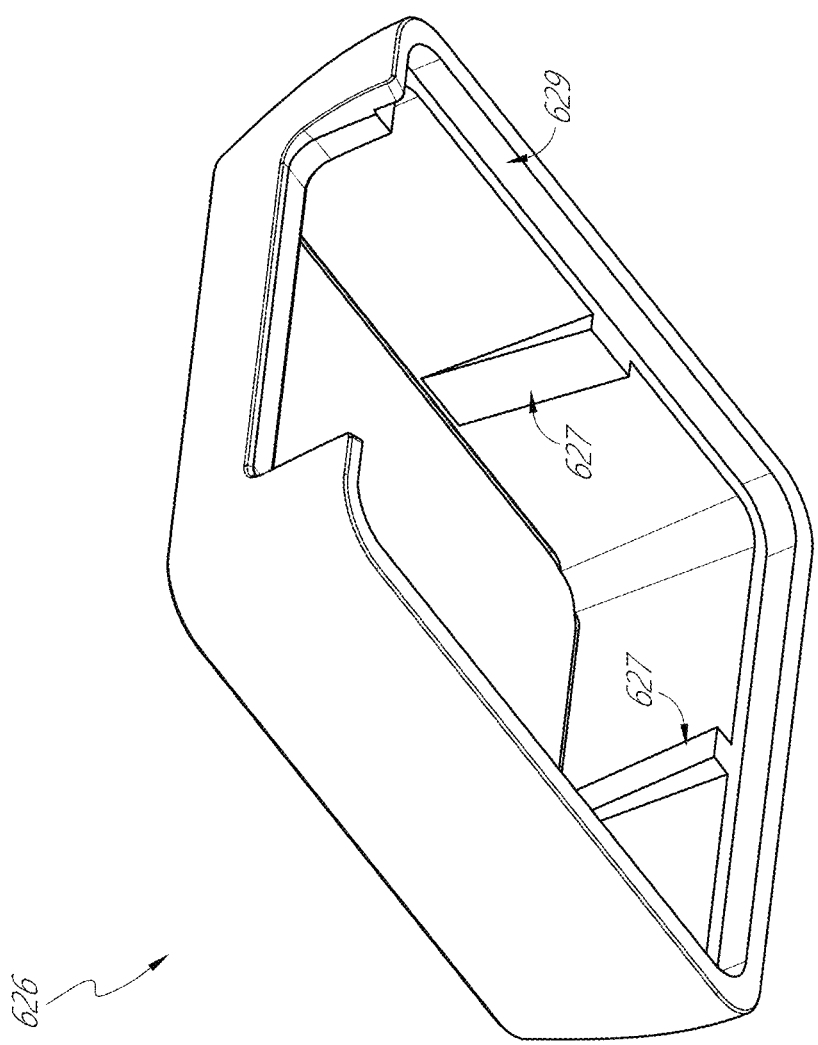
FIG. 6G illustrates an example outer shell of the graphics processing unit of the patient monitoring systems of FIGS. 2A-2B and 3A-3B.

As shown in FIG. 6G, the outer shell 626 can have four side walls defining a central opening. The outer shell 626 can also be generally a trapezium in its longitudinal cross-section such that it has a wider base. On the inner surface of the side walls of the shell 626, one or more ridges 627 can be disposed at locations corresponding to the locations of the grooves 621 on the housing 624. The ridges 627 can be shaped as wedges and the grooves 621 can correspondingly have a wider base and a narrower apex, such that the shell 626 can be slidably disposed onto the housing 624 in only one direction. The shapes of the ridges and grooves are not limiting. The number and location(s) of the ridges and grooves are also not limiting.

The shell 626 can also have a base portion 629 having a greater internal diameter than a remainder of the shell 626. The base portion 629 can have a predetermined depth that is substantially the same as the thickness of the base 628 of the housing 624, and/or an internal diameter that is substantially the same as the outer diameter of the housing base 628. When the shell 626 is slidably disposed onto the housing 624, the housing base 628 can be received in the base portion 629 of the shell 626. The relative shapes and sizes of the grooves 621 and the ridges 627, and/or the relative shapes and sizes of the base portion 629 and the housing base 628 can be configured such that the shell 626 is fixedly attached to the housing 624 by friction. An external force can be applied to overcome the friction so as to remove the shell 626 from the housing 624. The shell 626 can also be fixedly attached to the housing 624 by other attachment methods, such as adhesives, magnets, ball detents, and the like.

The shell 626 can protect the graphics processing unit 622 by reducing the likelihood of liquid drops from entering the housing 624 via the vent openings 625. The shell 626 can shield the vent openings 625 from splashes of liquid from the left and right sides. The shell 626 can also direct liquid drops falling onto the graphics processing unit 622 away from the vent openings. For example, the shell 626 can have a cross-section of a trapezium so that when the graphics processing unit 622 is in use, the top side wall of the shell 626 can have a slope (see FIGS. 6A and 6D). Further, the outer surface of the shell 626 can be a smooth surface. Accordingly, liquid drops can slide down the slope in a trajectory (such as shown by the arrows in FIGS. 6A and 6D) that is away from the graphics processing unit 622. As shown in FIG. 6D, liquid drops can still be directed away from the housing 624 even though the outer shell 626 may not enclose the housing 624 along its entire height such that the front surface of the housing stands proud of a front surface of the outer shell 626. The gaps between the shell 626 and the housing 624 can allow the shell 626 to protect the housing 624 from liquid drops without compromising the air flow through the interior of the housing 624 to dissipate heat generated by the processors inside the housing 624. The shell 626 can also have an opening 642 on its bottom side wall so as to allow access to the connection ports on the housing 624.

Example Display Racks with Improved Heat Dissipation

Heat dissipation can also be important in the multi-parameter monitoring device racks as the device racks disclosed herein can have its own processing units and/or host processing units in individual patient-monitoring modules. These processing units can generate heat when in use.

Figure 7B:
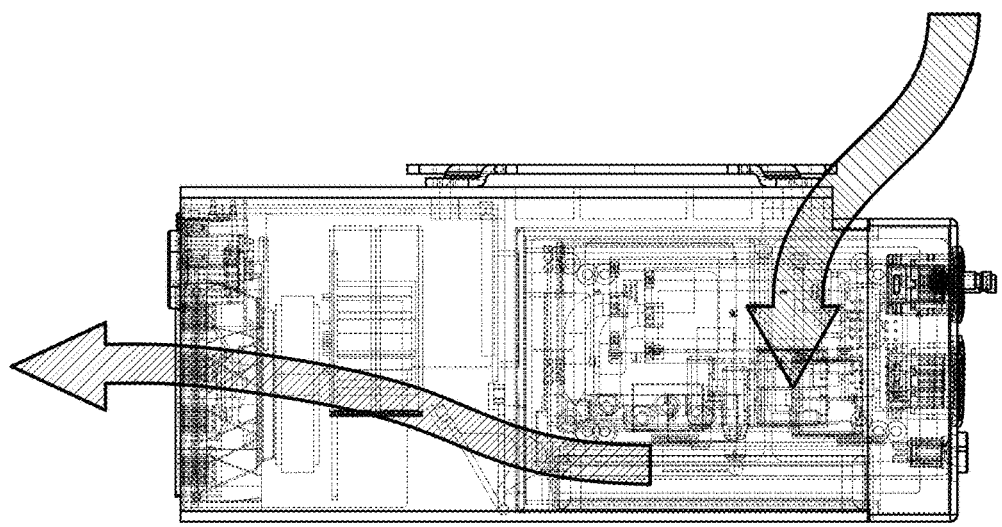
FIGS. 7A-7E illustrate example heat dissipation and/or drip-proof features of a device rack of the patient monitoring system of FIGS. 1A-3B.
Figure 7A:
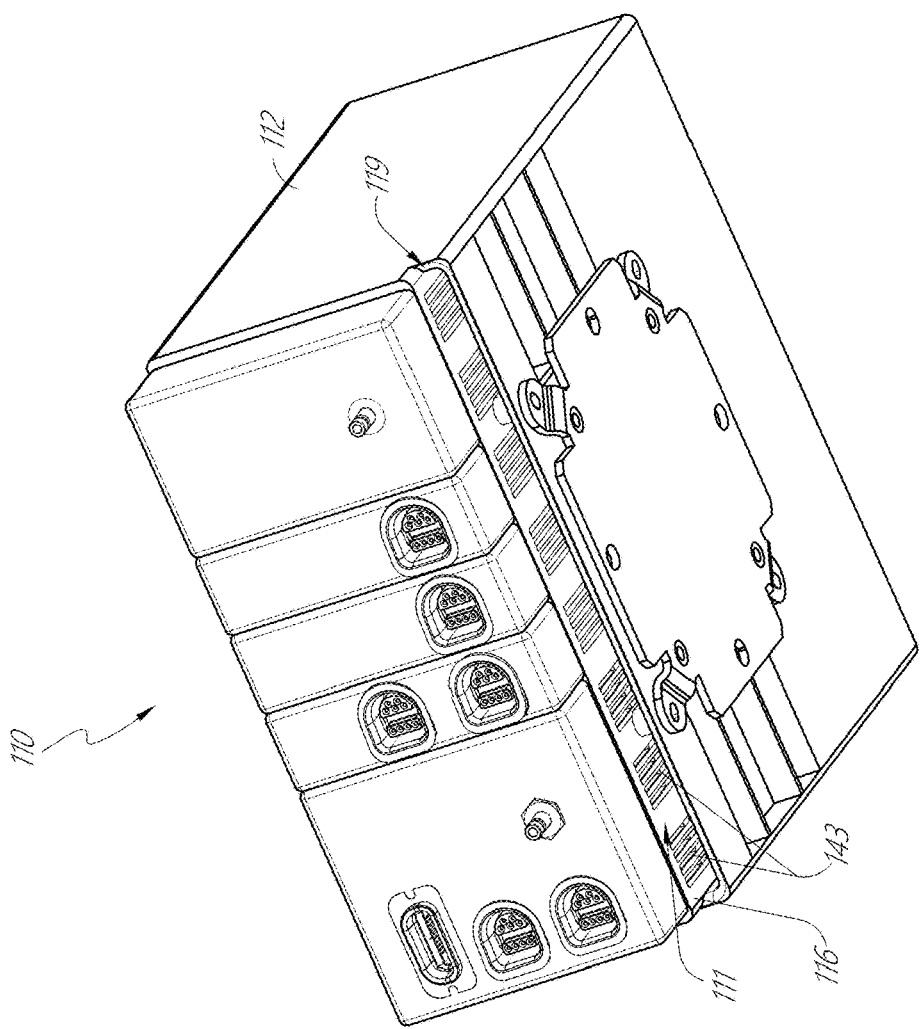

As shown in FIGS. 7A-7B, the device rack 110 in FIGS. 1A-1E can have a housing 112 sized to leave a gap 111 between an inner wall of the housing 112 and a dock housing 116 configured for receiving the patient monitor modules. As described above with reference to FIGS. 1A-1E, the device rack 110 can have a fan 113 at or near a back side of the housing 112. The signal processing unit 114 of the device rack 110 can be disposed between the dock housing 116 and the fan 113. When the fan 113 is turned on, for example, by a controller in the device rack 110, cool air, such as air at ambient and/or room temperature, can enter the multi-parameter monitoring device rack 110 via the gap 111, as shown by the incoming arrow in FIG. 7B. The outgoing arrow in FIG. 7B can show heated air leaving the multi-parameter monitoring device rack 110 after the air has passed through the processors in the device rack 110, including the signal processing unit 114 and/or the processers in the patient monitor modules. The air can exit the housing 112 via air outflow openings 144 of the fan 113 (see FIGS. 1E and 1G). The air flow path through the device rack housing 112 can be more efficient in dissipating the heat in the housing 112 than heat exchanges between air inside and outside the device rack housing via vent openings on only one side of the housing.

As shown in FIG. 7A, the dock housing 116 can also have a plurality of vent openings 143. The openings 143 can be near the gap 111 and be adjacent to the air flow path. The vent openings 143 on the dock housing 116 can allow cooling air to reach the patient monitor modules received in the device rack 110 to cool the processors in the patient monitor modules.

Figure 7C:
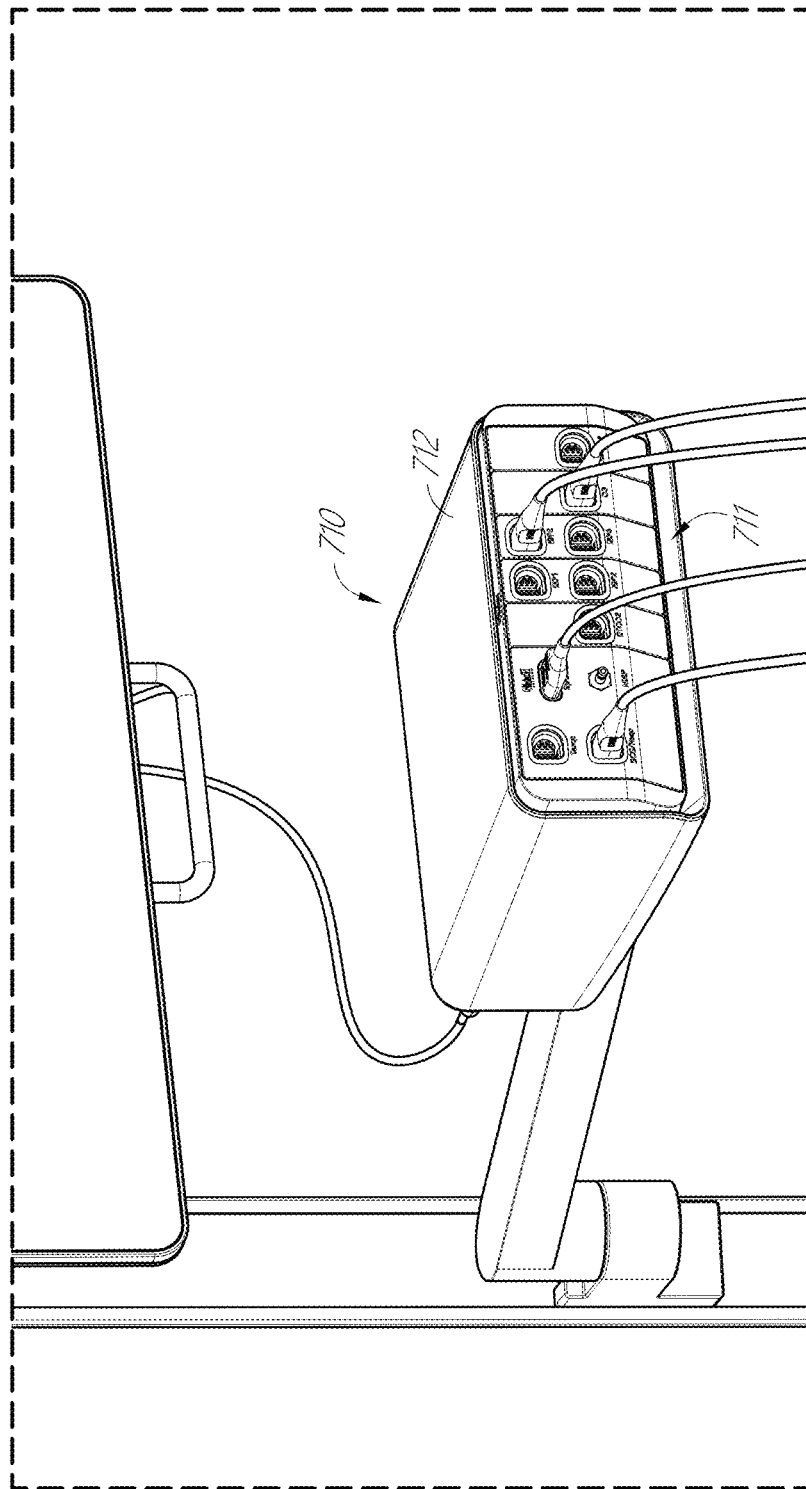
Figure 7D:
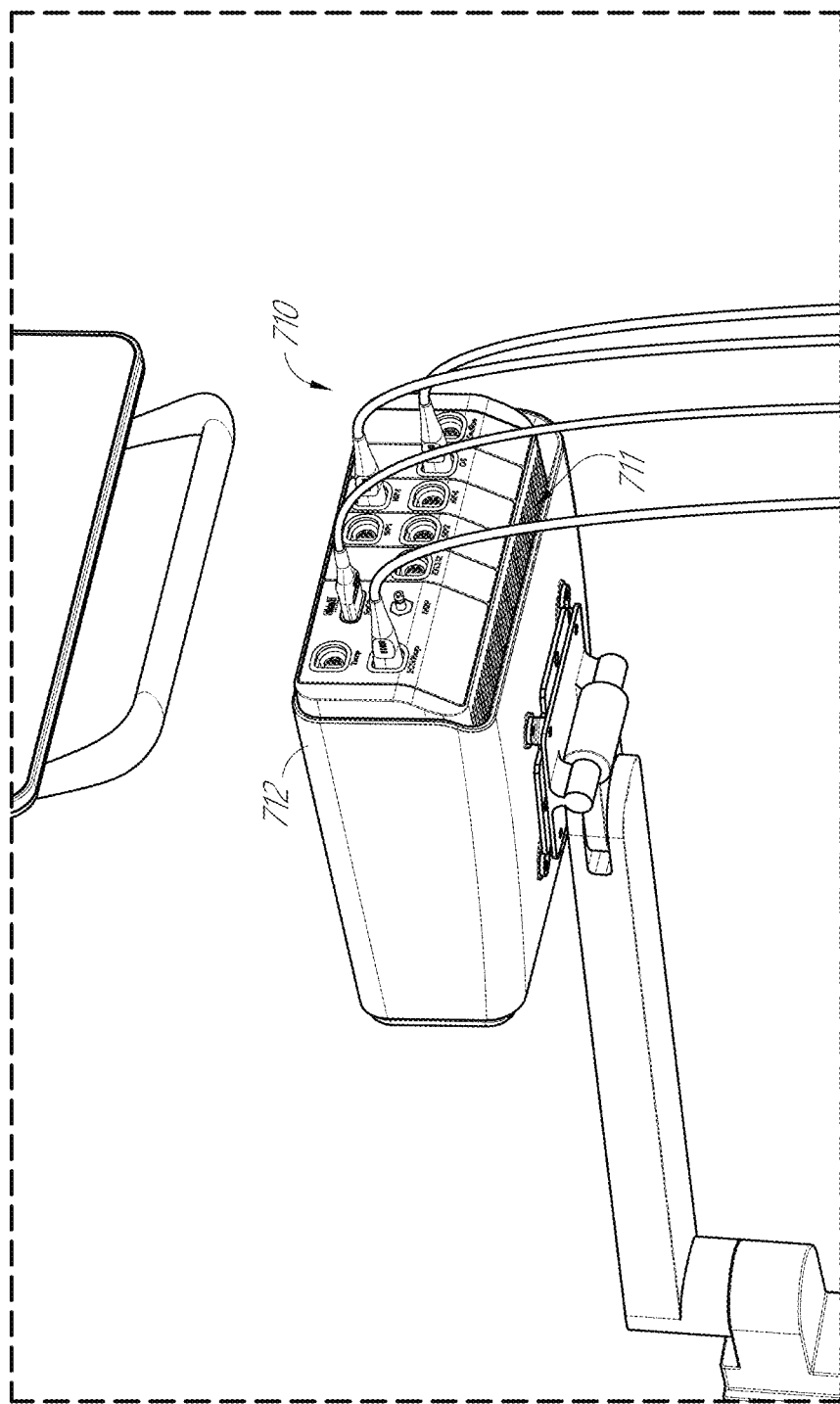
Figure 7E:
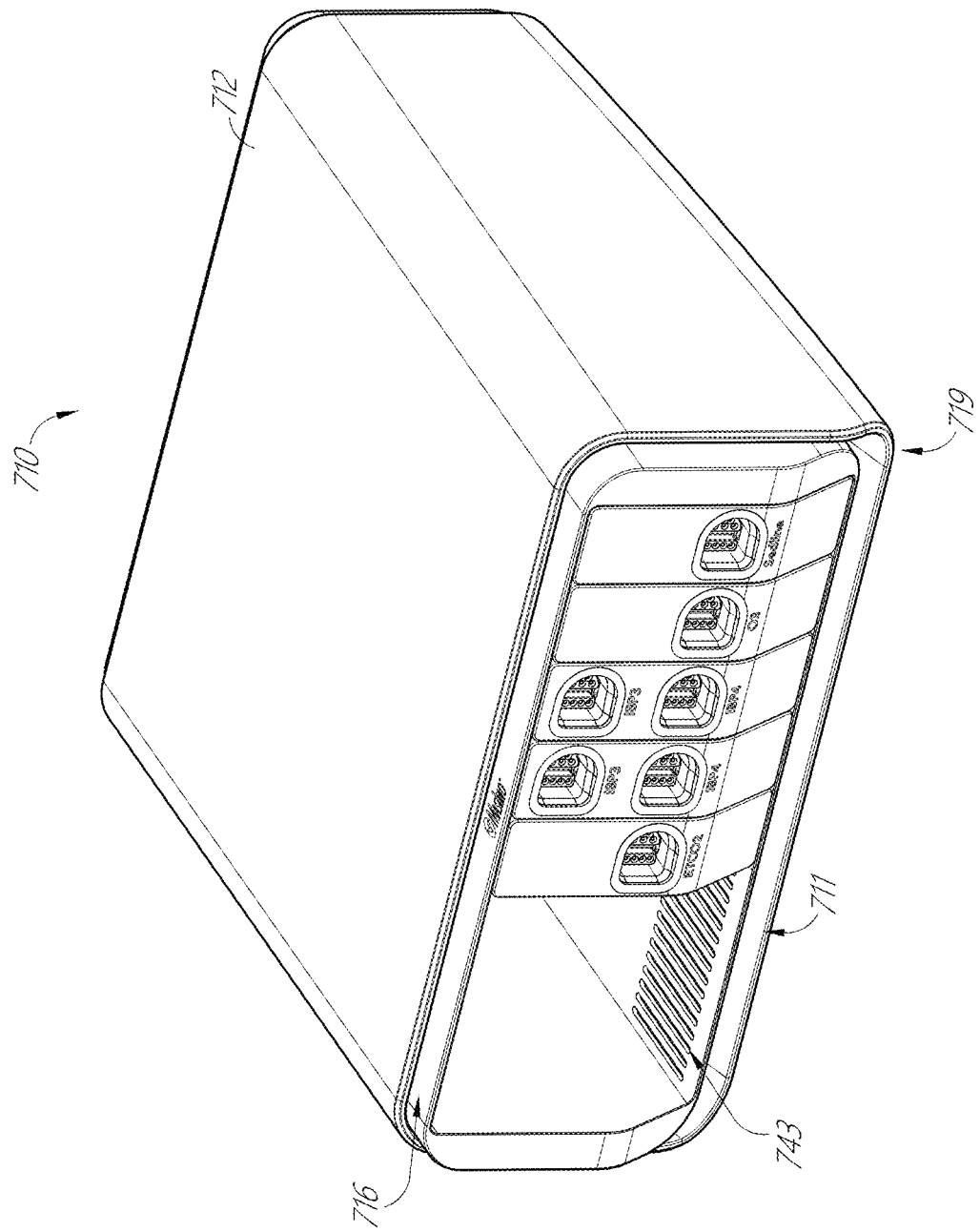

As illustrated in FIGS. 7C-7E, the device rack 710, which can be the device 210, 310 as shown in FIGS. 2A-3B, can also have a gap 711 between an inner wall of the housing 712 and the dock housing 716 of the device rack 710. Accordingly, a same or similar air flow path as shown in FIG. 7B can be generated in the device rack 710 to cool the processors in the housing 712, including the signal processing unit and/or the processers in the patient monitor modules. As shown in FIG. 7E, the dock housing 716 can also have a plurality of vent openings 743. The openings can be near the gap 711 and be adjacent to the cooling air flow path. The vent openings 743 on the dock housing 716 can allow cooling air to reach the patient monitor modules received in the device rack 710 to cool the processors on the patient monitor modules.

As illustrated in FIGS. 7A and 7E, the device racks 110, 710 can also have drip-proof features. In the device rack 110, the gap 111 can be located on the front side of the housing 112 that has a recessed portion 119. In the device rack 710, the gap 711 can be located on the front side of the housing 712 that has a beveled portion 119. The recessed portion 119 and the beveled portion 719 can result in the remainder of the device rack housing 112, 712 extending over the gap 111, 711 when in use. The reminder of the device rack housing 112, 712 can shield the gap 111, 711 from liquid drops. In the device rack 110, 710, the dock housing 116, 716 can also be sized so that when a patient monitor module is received into the dock housing 116, 716, a portion of the module extends outward from the front side of the device rack 110, 710 so that the portion of the module can hang over the gap 111, 711. The overhanging modules can also reduce the likelihood of liquid drops entering into the gap 111, 711. In the device rack 710, the dock housing 710 can also extend outward from the front side of the device rack housing 712. Even when the dock housing 716 is not fully occupied by patient monitor modules, the dock housing 716 can extend over the gap 711 to reduce the likelihood of liquid drops entering the gap 711.

The device rack 710 can also have the same or similar drip-proof features in the graphics processing unit as described above with reference to FIGS. 6A-6G. For example, the vent openings (see 244 in FIG. 2B and 344 in FIG. 3B) on the back side of the device rack 710 can be located on an inner cover. A top surface of the housing 712 of the device rack 710 can have a slope configured to allow liquid drops to slide off from the housing in a trajectory away from inner cover. Accordingly, the housing 712 of the device rack 710 can be configured to reduce the likelihood of liquid drops entering the vent openings (see 244 in FIG. 2B and 344 in FIG. 3B) and/or the speaker (see 217 in FIG. 2B and 317 in FIG. 3B).

Example Dual-Use Patient Monitor Modules

Figure 8A:
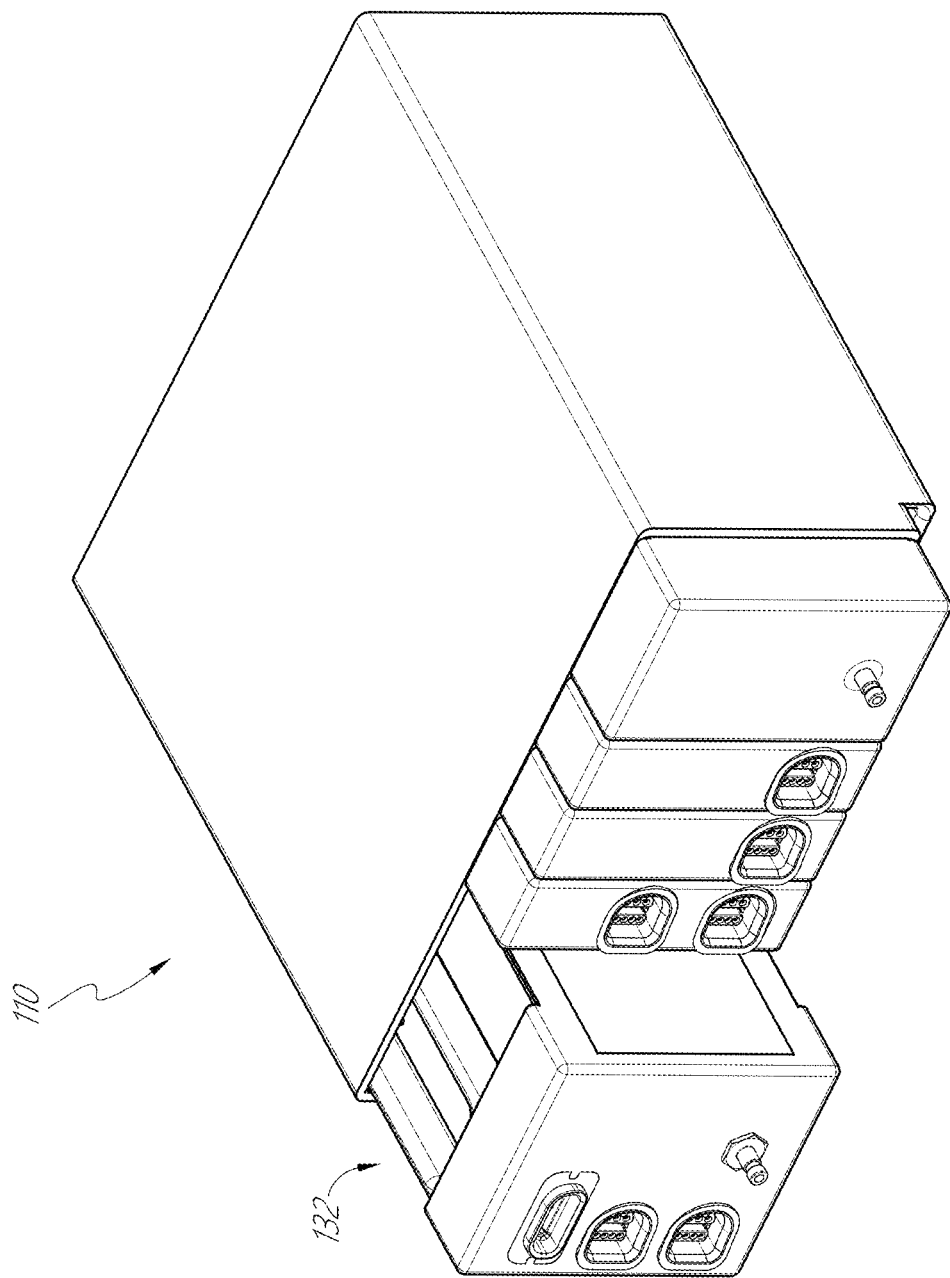
FIG. 8A illustrates the device rack of the patient monitoring system of FIGS. 1A-1B with an example dual-use patient monitor module partially removed.
Figure 8C:
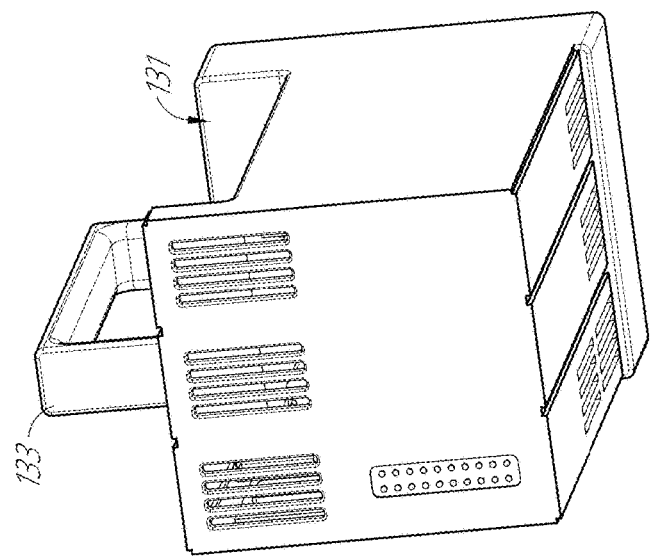
FIGS. 8B and 8C illustrate the example dual-use patient monitor module of FIG. 8A.
Figure 8B:
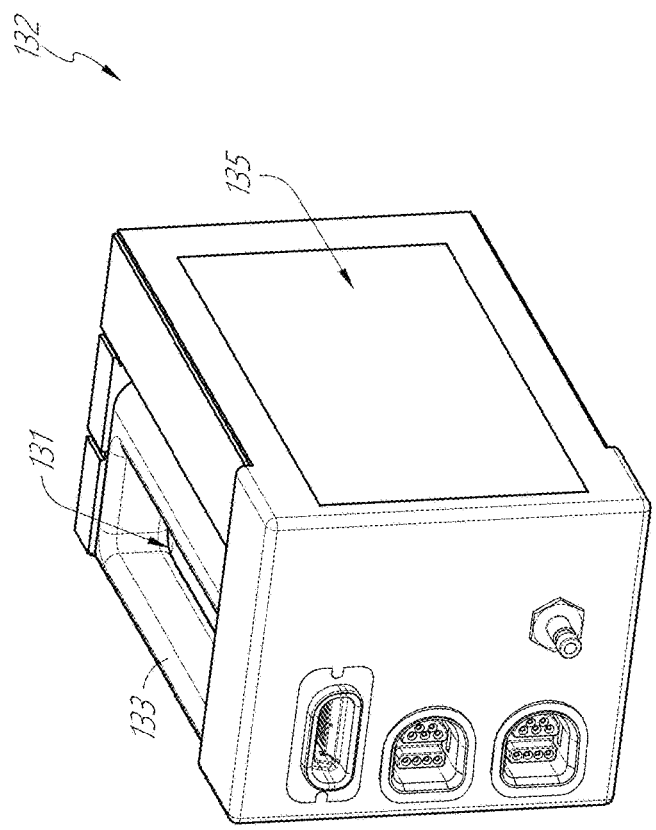

FIGS. 8A-8C show a dual-use patient monitor module 132 configured to be docked into the device rack 110 in FIGS. 1A-1H. FIGS. 8B and 8C illustrate the dual-use patient monitor module 132 in isolation. The dual-use patient monitor module 132 can have its own display unit 135 in addition to the one or more sensor ports and processing units, and can function as a stand-alone small portable patient monitoring device. The display unit 135 can be integrated into the housing of the dual-use module 132. The display unit 135 can be in communication with the processing unit of the dual-use module 132 to display the one or more parameters measured by the sensor(s) connected to the dual-use module 132. The dual-use module 132 can have a handle 133 on a housing of the module 132. As shown in FIGS. 8A and 8B, when the dual-use patient monitor module 132 needs to be inserted into the multi-parameter patient monitoring device rack 110, the handle 133 can be folded down into a retracted position. The housing of the dual-use module 132 can have a recess or groove 131 configured to receive the handle 133 when the handle 133 is folded down into the retracted position. When the handle 933 is in the retracted position, the handle 933 does not protrude outward from an outer wall of the module 931. This configuration can allow the housing of the dual-use module 132 to have a smooth outer profile compatible with the modular dock size of the multi-parameter patient monitoring device rack 110. As shown in FIG. 8C, when the dual use module 132 is used as a stand-alone patient monitoring device, the handle 133 can be rotated to an upright position, or an extended position, to enhance portability of the dual-use module 132. A healthcare professional can hand-carry the dual-use module 132 to various locations by holding onto the handle 133, which is more ergonomic than holding onto the housing of the module 132.

Figure 9:
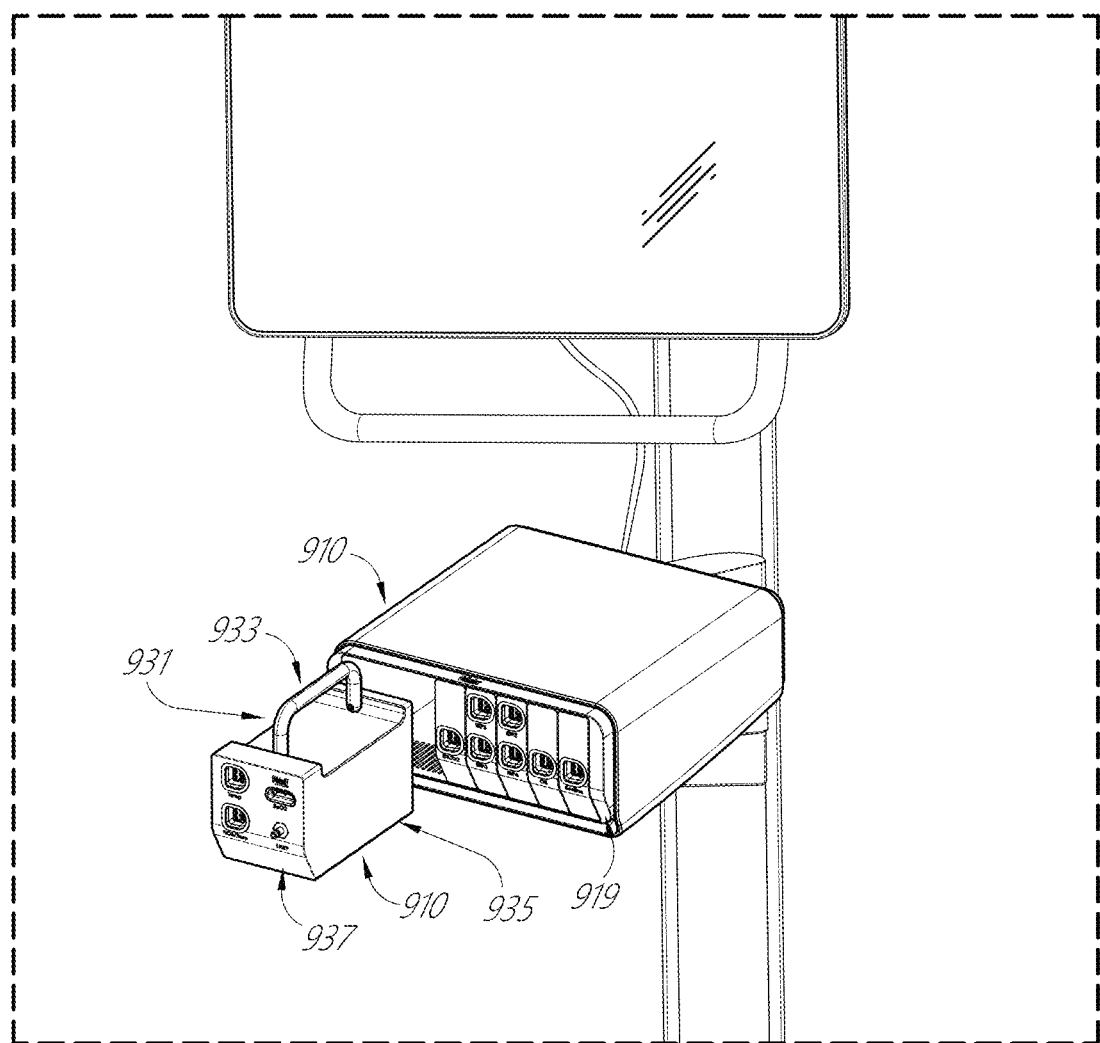
FIG. 9 illustrates another example dual-use patient monitor module configured to be received by a device rack disclosed herein.

FIG. 9 illustrates a dual-use patient monitor model 932 configured to be docked into a device rack 910, which can be the device rack 210, 310 in FIGS. 2A-3B. The dual-use patient monitor model 932 can have any of features of the dual-use patient monitor model 132 described above and any other features described below. The dual-use patient monitor module 932 can have its own display unit 935 in addition to the one or more sensors and processing units, and can function as a stand-alone small portable patient monitoring device. The dual-use module 932 can have a handle 933. When the dual-use patient monitor module 932 needs to be inserted into the multi-parameter patient monitoring device rack 910, the handle 933 can be folded down into a retracted position. The housing of the dual-use module 932 can have a recess or groove 931 configured to receive the handle 933 when the handle 933 is folded down into the retracted position. When the handle 933 is in the retracted position, the handle 933 does not protrude outward from an outer wall of the module 931. This configuration can allow the housing of the dual-use module 932 to have a smooth outer profile compatible with the modular dock size of the multi-parameter patient monitoring device rack 910. The module 932 can also have a beveled portion 937 on its front surface so as to align with a beveled portion 919 on the front surface of the device rack 910. When the dual-use module 932 is used as a stand-alone patient monitoring device, the handle 933 can be rotated to an upright position, or an extended position, to enhance portability of the dual-use module 932.

Example Device Racks with Modular Docks

Figure 10:
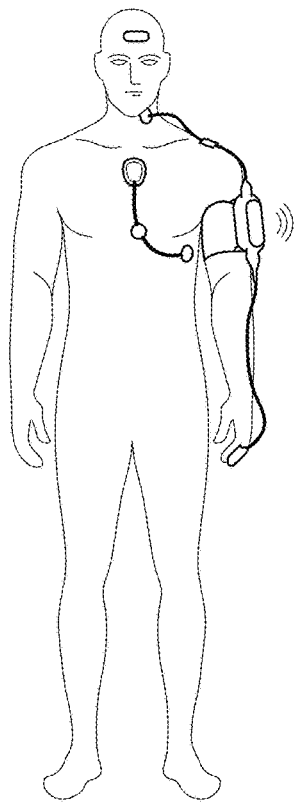
FIG. 10 illustrates schematically example multi-parameter patient monitoring systems for various clinical applications.
Figure 10:
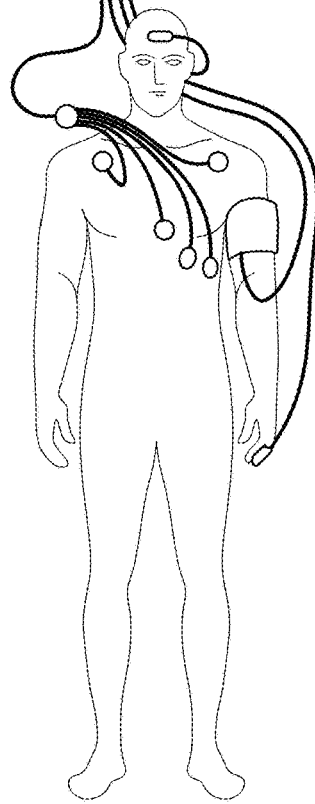
Figure 10:
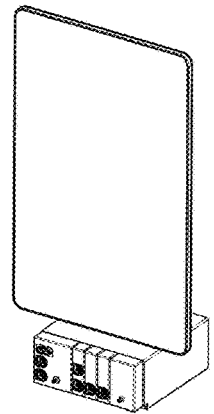
Figure 10:
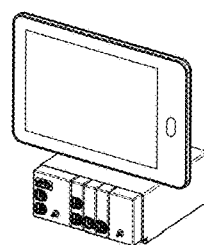
Figure 10:
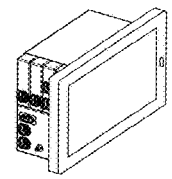
Figure 10:
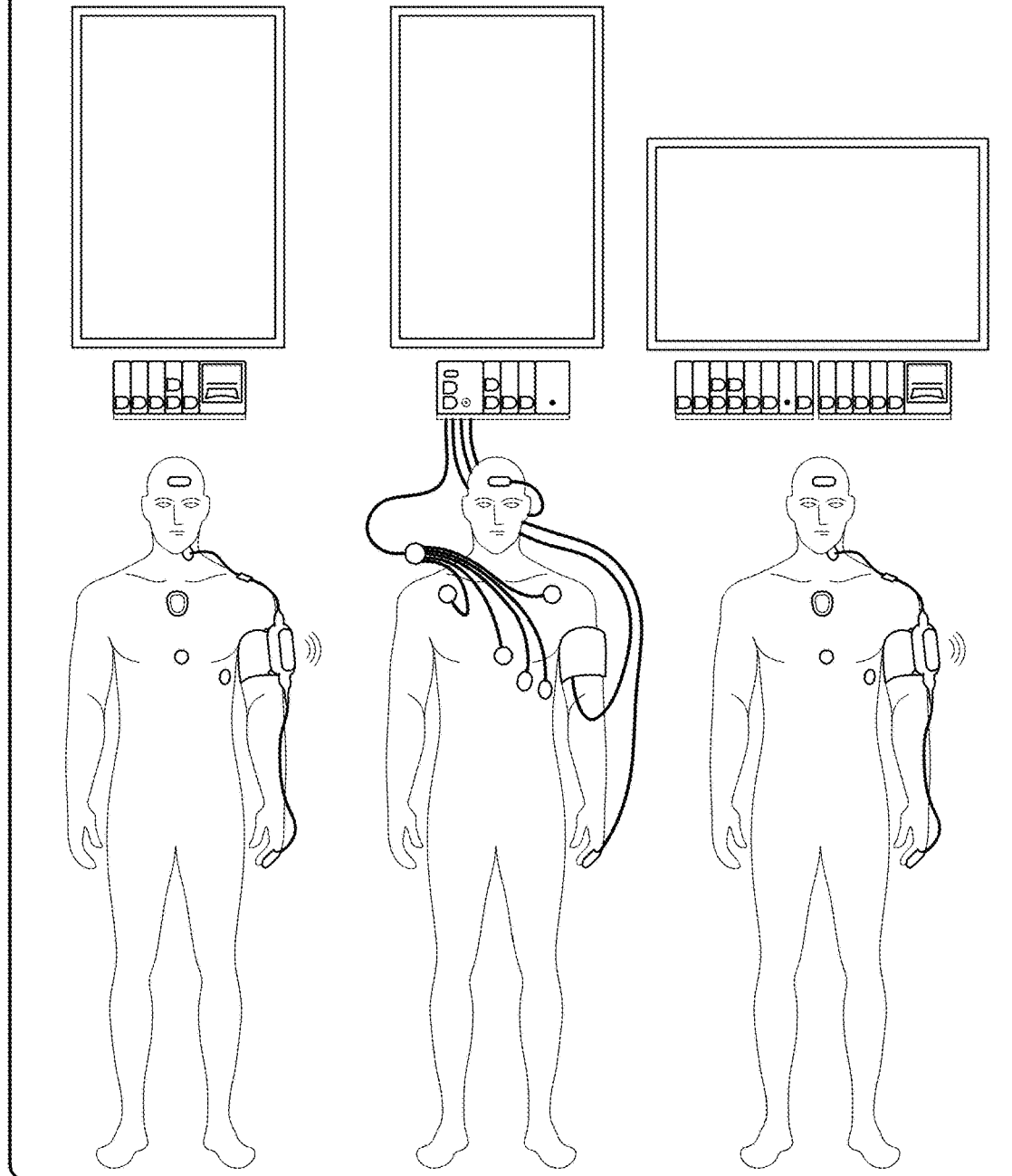

As shown in FIG. 10, a multi-parameter patient monitoring device rack 110 disclosed herein can be in communication with a separate display unit 120 disclosed herein. The multi-parameter monitoring system described herein can be used in low acuity settings, such as in a step-down unit, emergency center, or surgery center, and/or in high acuity settings, such as neonatal ICU, medical ICU, Cardiothoracic (CT) ICU, and neuro and trauma ICU. The display unit 120 can have varying display area sizes. The processing unit of the device rack 110 can also wirelessly communicate with a wearable patient monitoring device so as to display values of the parameters monitored by the wearable device on the display unit 120.

Figure 11:
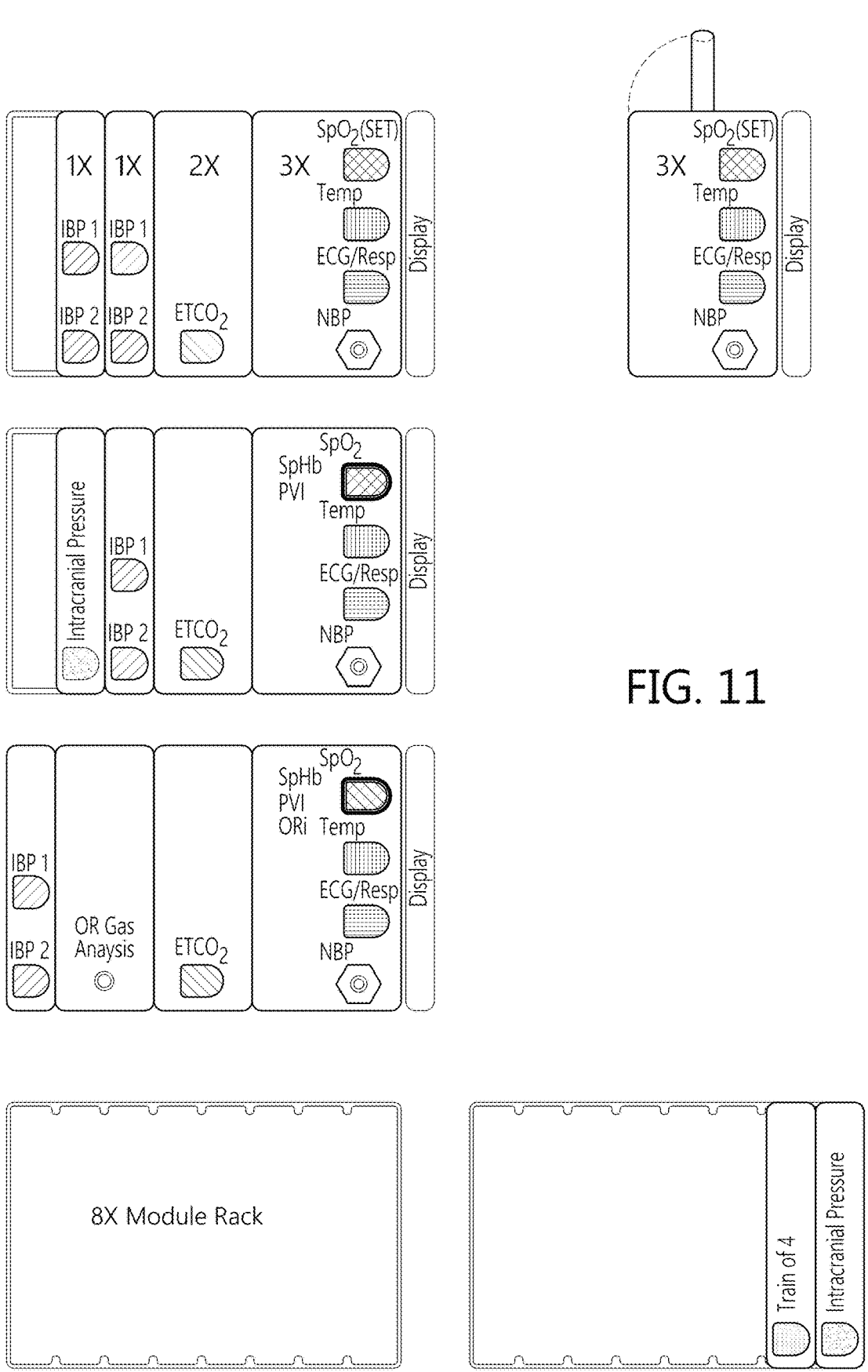
FIG. 11 illustrates schematically various combinations of patient monitoring modules docked into a plurality of modular patient monitoring device racks.
Figure 11:
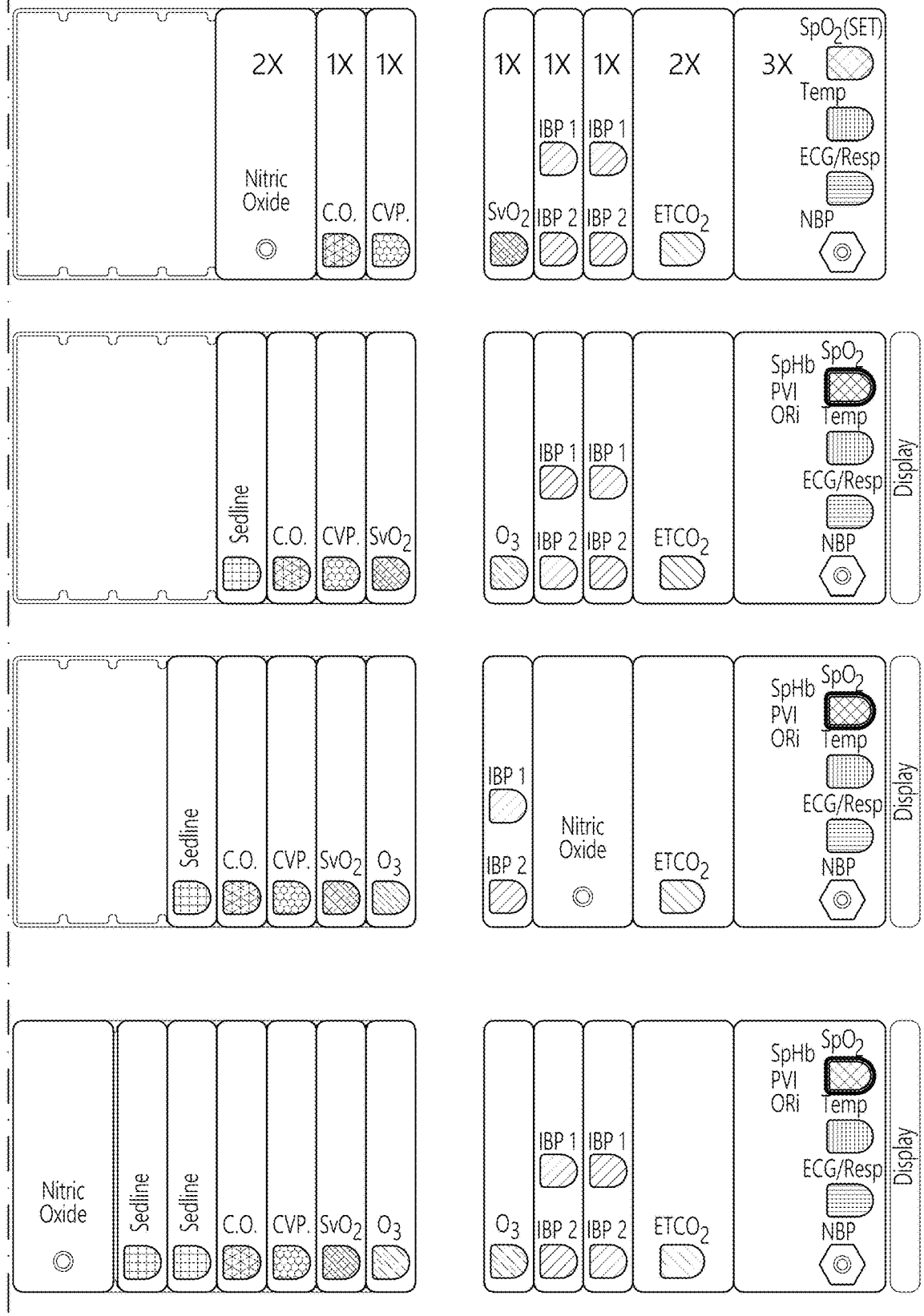

Turning to FIG. 11, the parameters of interest can depend on the setting in which the multi-parameter monitoring system is used. Further, while one multi-parameter patient monitoring device rack may be sufficient for measuring a basic parameter set in low acuity systems, two or more multi-parameter patient monitoring device racks may be required for high acuity systems because of the number of parameters that require monitoring. Using the multi-parameter monitoring device rack 110 as an example, each device rack can have a plurality of (for example, sixe, eight, or more) modular docks. The plurality of modular docks 116 can receive the patient monitor modules or bricks 130, 132, 134, 136, 138. The patient monitoring modules 130, 132, 134, 136, 138 can have a size that is the same as the modular dock size or multiples of the dock size. As shown in FIG. 1G, the patient monitoring modules 130, 132, 134, 136, 138 can have a size configured for being received in one, two, three modular docks, and so on. The modules 134, 136, 138 can have a size for being received by one module dock. The module 130 can have a size for being received by two modular docks. The module 132 can have a size for being received by three modular docks. As another example, in FIG. 9, the dual-use patient module 932 can have a size for being received by three modular docks of the device rack 910.

TERMINOLOGY

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A computer processing unit of a multi-parameter patient monitoring system with improved heat dissipation, the processing unit comprising:
   a first housing having a front side, a back side, and a side surface extending between the front and back sides, the housing comprising a plurality of vent openings;
   a second housing extending around the side surface of the first housing and is spaced apart from an outer wall of the side surface to define a gap, at least a portion of the plurality of vent openings of the first housing being at the side surface and adjacent to the gap;
   one or more hardware processors within the first housing; and
   a fan located within the first housing, wherein, when activated, the fan is configured to draw pressurized air into the gap, the pressurized air flowing over the one or more hardware processors before exiting through at least some of the plurality of vent openings that are located away from the gap.

2. The computer processing unit of claim 1, wherein the fan is located near one or more of the plurality of openings.

3. The computer processing unit of claim 1, wherein the plurality of vent openings are located at the side surface.

4. The computer processing unit of claim 3, wherein the plurality of vent openings are located on opposing sides of the side surface.

5. The computer processing unit of claim 1, wherein the one or more hardware processors comprise one or more graphics processors configured to communicate with a second processing unit of the multi-parameter patient monitoring system to receive values of the one or more physiological parameters, the second processing unit located away from the device.

6. The computer processing unit of claim 1, wherein at least some of the vent openings are located on the back side.

7. The computer processing unit of claim 1, wherein the first housing comprising a plurality of docking stations configured to receive one or more patient monitor modules, the plurality of patient monitor modules each configured for connecting to one or more sensors so as to measure one or more physiological parameters.

8. The computer processing unit of claim 7, wherein the plurality of docking stations comprise docking stations of different sizes.

9. The computer processing unit of claim 7, wherein the plurality of docking stations are located adjacent the gap.

10. A graphics processing unit of a multi-parameter patient monitoring system with improved heat dissipation, the graphics processing unit comprising:
a first housing having a front side, a back side, and a side surface extending between the front and back sides, the side surface comprising a plurality of vent openings;
a second housing extending around the side surface of the first housing and is spaced apart from an outer wall of the side surface to define a gap, at least a portion of the plurality of vent openings being adjacent to the gap;
one or more graphics processors within the first housing; and
a fan located in the first housing, wherein, when activated, the fan is configured to draw pressurized air into the gap, the pressurized air flowing over the one or more graphics processors before exiting through the plurality of vent openings.

11. The graphics processing unit of claim 10, wherein the fan is located near one or more of the plurality of openings.

12. The graphics processing unit of claim 10, wherein the plurality of vent openings are located on opposing sides of the side surface.

13. The graphics processing unit of claim 10, wherein the one or more graphics processors are configured to communicate with a second processing unit of the multi-parameter patient monitoring system to receive values of the one or more physiological parameters, the second processing unit being separate from the graphics processing unit.

14. The graphics processing unit of claim 10, wherein the gap extending around a perimeter of the side surface.

15. A device rack of a multi-parameter patient monitoring system with improved heat dissipation, the device rack configured to electrically communicate with a graphics processing unit separate from the device rack, the device rack comprising:
a device rack housing having a front side, a back side, and a side surface extending between the front and back sides, the back side comprising a plurality of vent openings;
a docking compartment comprising a plurality of docks configured to receive a plurality of patient monitor modules, the plurality of patient monitor modules each configured for connecting to one or more sensors so as to measure one or more physiological parameters, wherein the dock compartment is located within the device rack housing and is spaced apart from an inner wall of the device rack housing to define a gap, the dock compartment comprising a plurality of vent openings adjacent to the gap;
a processor unit configured to receive and process data from the plurality of patient monitor modules, the processing unit being located closer to the back side than the docking compartment; and
a fan located in the housing, wherein, when activated, the fan is configured to draw pressurized air into the gap, the pressurized air flowing over the processor unit before exiting through the plurality of vent openings on the back side.

16. The device rack of claim 15, wherein the docking compartment comprises an inner housing separate from the device rack housing.

17. The device rack of claim 16, wherein a portion of the docking compartment extends outward from the device rack housing on the front side.

18. The device rack of claim 15, wherein a plurality of walls of the docking compartment is integral with the device rack housing.

19. The device rack of claim 15, wherein the plurality of patient monitor modules are configured to be received via the front side.

20. The device rack of claim 15, wherein the fan is located closer to the back side than the docking compartment.

* * * * *